US011285455B2

(12) United States Patent
Yoon et al.

(10) Patent No.: US 11,285,455 B2
(45) Date of Patent: Mar. 29, 2022

(54) ORGANIC-INORGANIC HYBRID NANOPOROUS MATERIAL CONTAINING INTRAMOLECULAR ACID ANHYDRIDE FUNCTIONAL GROUP, COMPOSITION FOR ADSORPTION COMPRISING THE SAME, AND USE THEREOF FOR SEPARATION OF HYDROCARBON GAS MIXTURE

(71) Applicant: KOREA RESEARCH INSTITUTE OF CHEMICAL TECHNOLOGY, Daejeon (KR)

(72) Inventors: Ji Woong Yoon, Daejeon (KR); Jong San Chang, Daejeon (KR); Young Kyu Hwang, Daejeon (KR); Kyung Ho Cho, Gyeonggi-do (KR); U Hwang Lee, Daejeon (KR); Su Kyung Lee, Daejeon (KR); Ji Sun Lee, Busan (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 16/342,937

(22) PCT Filed: Oct. 17, 2017

(86) PCT No.: PCT/KR2017/011461
§ 371 (c)(1),
(2) Date: Apr. 17, 2019

(87) PCT Pub. No.: WO2018/074815
PCT Pub. Date: Apr. 26, 2018

(65) Prior Publication Data
US 2019/0291075 A1 Sep. 26, 2019

(30) Foreign Application Priority Data
Oct. 17, 2016 (KR) .................. 10-2016-0134653

(51) Int. Cl.
| | |
|---|---|
| *B01J 20/22* | (2006.01) |
| *B01D 53/047* | (2006.01) |
| *B01J 20/34* | (2006.01) |
| *C07C 7/12* | (2006.01) |
| *B01D 53/04* | (2006.01) |
| *B82Y 30/00* | (2011.01) |
| *B82Y 40/00* | (2011.01) |

(52) U.S. Cl.
CPC ............ *B01J 20/226* (2013.01); *B01D 53/04* (2013.01); *B01D 53/047* (2013.01); *B01J 20/22* (2013.01); *B01J 20/3425* (2013.01); *B01J 20/3483* (2013.01); *B01J 20/3491* (2013.01); *B82Y 30/00* (2013.01); *B82Y 40/00* (2013.01); *C07C 7/12* (2013.01); *B01D 2253/204* (2013.01); *B01D 2256/24* (2013.01); *B01D 2257/7022* (2013.01); *Y02C 20/20* (2013.01)

(58) Field of Classification Search
CPC .................. B01D 53/04; B01D 53/047; B01D 2253/204; B01D 2256/24; B01D 2257/7022; B01J 20/22; B01J 20/3425; B01J 20/3483; B01J 20/3491; B82Y 30/00; B82Y 40/00; C07C 7/12; Y02C 20/20
See application file for complete search history.

(56) References Cited

U.S. PATENT DOCUMENTS

| | | | |
|---|---|---|---|
| 6,315,816 B1 | 11/2001 | Cho et al. | |
| 6,468,329 B2 | 10/2002 | Cho et al. | |
| 10,294,255 B1 * | 5/2019 | Tan | ........................ C07F 7/0812 |
| 10,675,608 B2 * | 6/2020 | Eddaoudi | ............. B01J 20/3265 |

(Continued)

FOREIGN PATENT DOCUMENTS

| | | |
|---|---|---|
| CN | 104056598 A | 9/2014 |
| FR | 2903981 A1 | 1/2008 |

(Continued)

OTHER PUBLICATIONS

Reimer et al. "Thermal post-synthetic modification of AI-MIL-53-COOH: systematic investigation of the decarboxylation and condesation reaction" Crystal Engineering Communications, 2012. (Year: 2012).*

(Continued)

*Primary Examiner* — Alexander R Pagano
(74) *Attorney, Agent, or Firm* — Brooks Kushman P.C.

(57) ABSTRACT

The present invention relates to an organic-inorganic hybrid nanoporous material, maintaining a nanoporous skeleton structure formed by coordination of an organic ligand containing an aromatic compound to a trivalent central metal ion, and further having an intramolecular acid anhydride functional group modified on the aromatic compound of the nanoporous skeleton structure, and thereby exhibits selectivity for olefins, and an adsorbent comprising the same. Specifically, the organic-inorganic hybrid nanoporous material of the present invention exhibits an excellent olefin-selective adsorption capacity through differences in adsorption equilibrium and adsorption rate, and thus can be usefully employed in the separation of C2-C4 hydrocarbons. Further, the olefins adsorbed to the organic-inorganic hybrid nanoporous material can be desorbed by purging of an inert gas which is not liquefied by way of mild vacuum conditions or compression, and thus, the organic-inorganic hybrid nanoporous material can be used to prepare olefins by separating C2-C4 hydrocarbon mixtures.

17 Claims, 8 Drawing Sheets

(56) References Cited

U.S. PATENT DOCUMENTS

| | | | | |
|---|---|---|---|---|
| 2008/0227634 | A1* | 9/2008 | Muller | F17C 11/00 502/402 |
| 2009/0042000 | A1* | 2/2009 | Schubert | C07C 63/307 428/219 |
| 2010/0006454 | A1* | 1/2010 | Gruenwald | F17C 11/007 206/0.7 |
| 2014/0199352 | A1* | 7/2014 | Lawton | A61K 8/0279 424/401 |
| 2015/0144085 | A1* | 5/2015 | Inubushi | C07C 63/28 123/1 A |
| 2015/0165415 | A1* | 6/2015 | Inubushi | B01D 53/02 546/2 |
| 2015/0231600 | A1* | 8/2015 | Rosseinsky | C07C 7/12 585/830 |
| 2016/0340595 | A1* | 11/2016 | Matteucci | C10L 3/10 |
| 2016/0340596 | A1* | 11/2016 | Matteucci | B01D 53/04 |
| 2019/0291075 | A1* | 9/2019 | Yoon | B01J 20/226 |
| 2020/0047114 | A1* | 2/2020 | Al-Maythalony | B01D 71/028 |

FOREIGN PATENT DOCUMENTS

| | | |
|---|---|---|
| JP | 2009521320 A | 6/2009 |
| KR | 100787210 B1 | 12/2007 |
| KR | 100828137 B1 | 5/2008 |
| KR | 1020080038191 A | 5/2008 |
| KR | 101105640 B1 | 1/2012 |
| KR | 101344698 B1 | 12/2013 |
| KR | 1020160036766 A | 4/2016 |

OTHER PUBLICATIONS

C. Serre et al., 124 Journal of the American Chemical Society, 13519-13526 (2002) (Year: 2002).*

Z. Bao et al., 9 Energy and Environmental Science, 3612-3641 (2016) (Year: 2016).*

J. Yoon et al., 49 Angewandte Chemie International Edition, 5949-5952 (2010) (Year: 2010).*

A. Ferreira et al., 167 Chemical Engineering Journal, 1-12 (2011) (Year: 2011).*

D. Olson et al., 108 Journal of Chemical Physics B, 11044-11048 (2004) (Year: 2004).*

K. Li et al., 131 Journal of the American Chemical Society, 10368-10369 (2009) (Year: 2009).*

N. Reimer et al., 14 CrystEngComm, 4119-4125 (2012) (Year: 2012).*

Bao, Zongbi et al., "Potential of microporous metal-organic frameworks for separation of hydrocarbon mixtures", Energy & Environmental Science, Aug. 2016, 9, 12, pp. 3612-3641, Royal Society of Chemistry, London, United Kingdom.

Bloch, Eric D. et al., "Hydrocardbon Separations in a Metal-Organic Framework with Open Iron(II) Coordination Sites", Science Magazine, Mar. 30, 2012, pp. 1606-1610, vol. 335, American Association for the Advancement ol Science, Washington D.C., United States.

Ferreira, Alexandre F.P. et al., "Suitability of Cu-BTC extrudates for propane-propylene separation by adsorption processes", Chemical Engineering Journal, 2011, pp. 1-12, vol. 167, Elsevier, Amsterdam, Netherlands.

Huang, Aisheng, et al., "Molecular-Sieve Membrane with Hydrogen Permselectivity: ZIF-22 in LTA Topology Prepared with 3-Aminopropyltriethoxysilane as Covalent Linker", InterScience, 2010, pp. 4958-4961, vol. 49, Wiley-Verlag GmbH & Co. KGaA, Weinheim, Germany.

International Search Report PCT/KR2017/011461, Prepared by the KR Patent Office, dated Jan. 31, 2018.

Kojtari, Arben et al., "Metal Organic Framework Micro/Nanopillars of Cu(BTC)-3H2O and Zn(ADC)-DMSO", Nanomaterials, Jun. 2015, pp. 565-576, vol. 5(2), MDPI, Basel, Switzerland.

Li, Kunhao et al., "Zeolitic Imidazolate Frameworks for Kinetic Separation of Propane and Propene", Journal of the American Chemical Society Communications, Jul. 10, 2009, pp. 10368-10369, vol. 131, No. 30, American Chemical Society, Washington D.C., United States.

Olson, David et al., "ITQ-12: A Zeolite Having Temperature Dependent Adsorption Selectivity and Potential for Propene Separation", Journal of Physical Chemistry B—J Phys Chem B, May 10, 2004, pp. 11044-11048, vol. 108, No. 30, American Chemical Society, Washington D.C., United States.

Ruthven, Douglas et al., "Adsorptive separation of light olefins from paraffins", Microporous and Mesoporous Materials Journal, Jan. 16, 2007, pp. 59-66, vol. 104, Elsevier, Amsterdam, Netherlands.

Serre, Christian, et al., "Very Large Breathing Effect in the First Nanoporous Chromium(III)-Based Solids: MIL-53 ar CRIII(OH)-{O2C-C6H4-CO2}-{HO2C-C6H4-CO2H}x-H2Oy", Journal of the American Chemical Society, Nov. 2002, pp. 13519-13526, vol. 124, American Chemical Society, Washington D.C., United States.

Rubes, et al., Adsorption of Propane and Propylene on CuBTC Metal-Organic Framework: Combined Theoretical and Experimental Investigation, The Journal of Physical Chemistry, Published Apr. 29, 2013, 9 pages.

Sumby, Christopher J., Bridging ligands comprising two or more di-2-pyridylmethyl or amine arms: Alternatives to 2,2_-bipyridyl-containing bridging ligands, Coordination Chemistry Reviews 255 (2011) 1937-1967.

IUPAC. Compendium of Chemical Terminology, 2nd ed.(the "Gold Book"). Compiled by A. D. McNaught and A. Wilkinson. Blackwell Scientific Publications, Oxford (1997). Onlineversion (2019-) created by S. J. Chalk. ISBN 0-9678550-9-8.https://doi.org/10.1351/goldbook.

Holister, Paul, Cristina Román Vas, and Tim Harper. "Nanoporous Materials." (2003).

* cited by examiner

[FIG. 1]
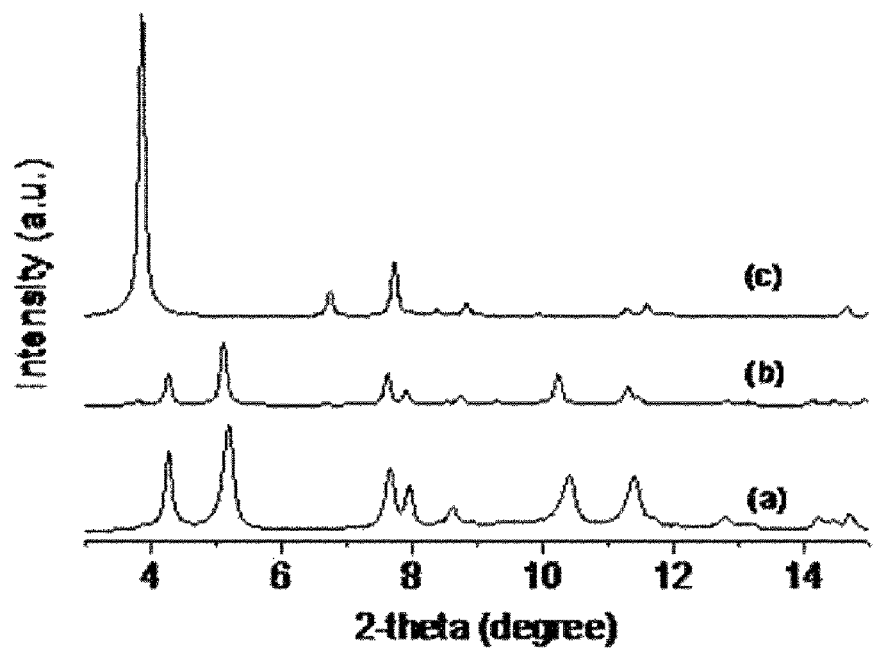

[FIG. 2]
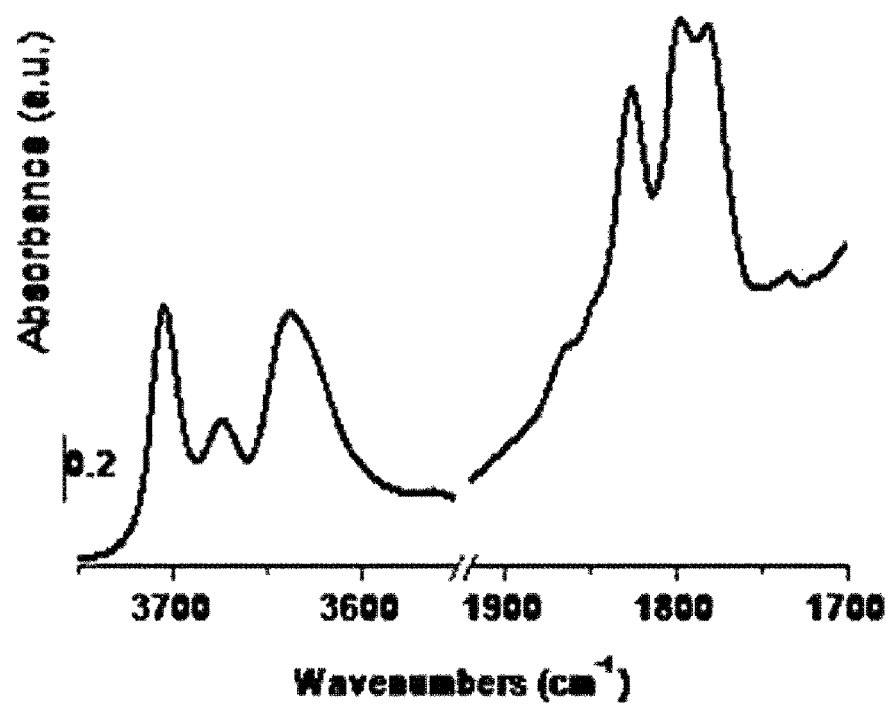

[FIG. 3]
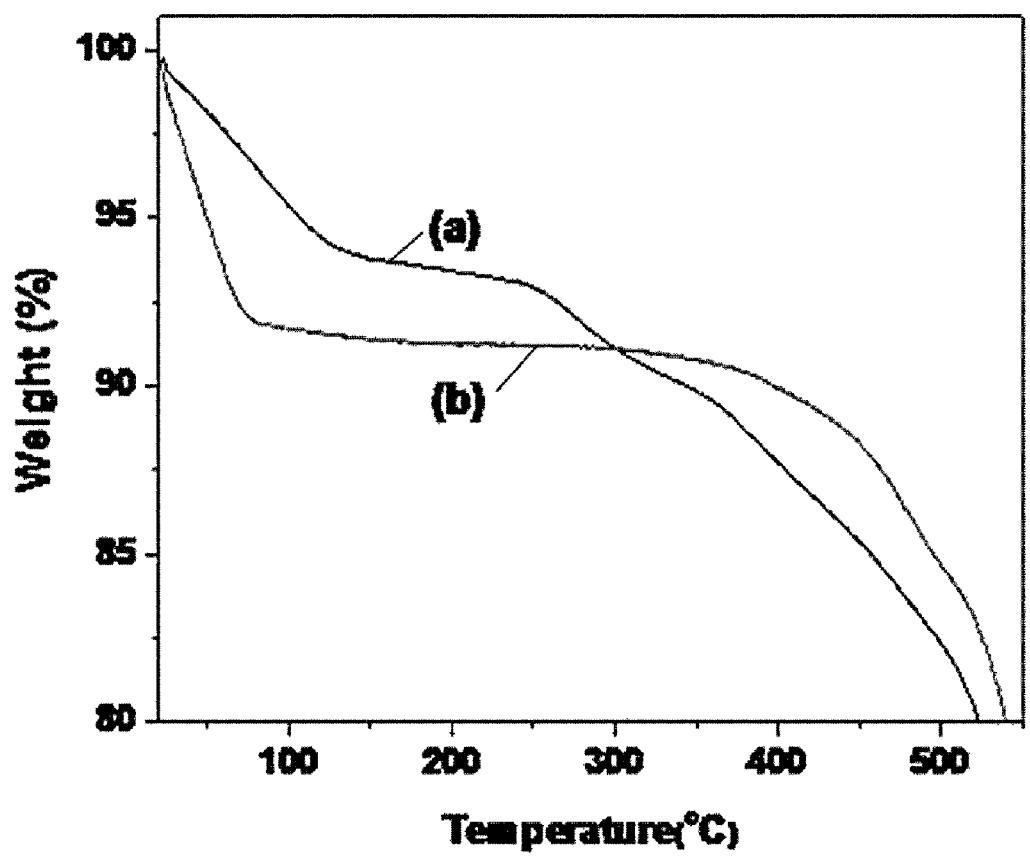

[FIG. 4]
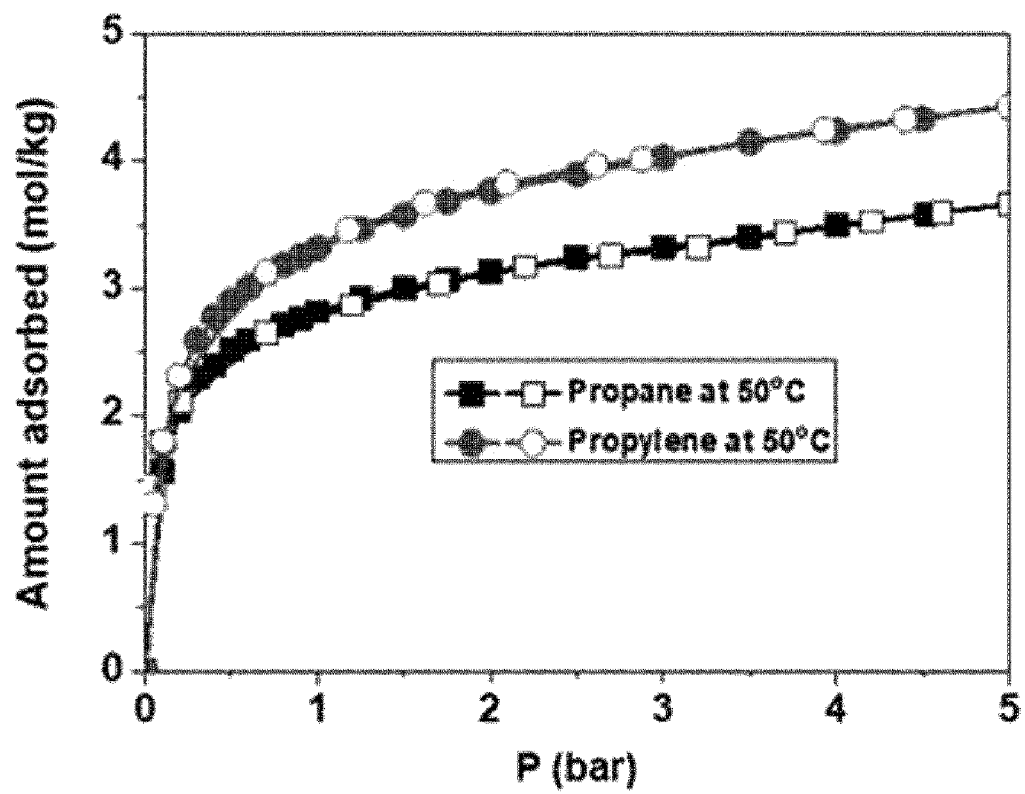

[FIG. 5]
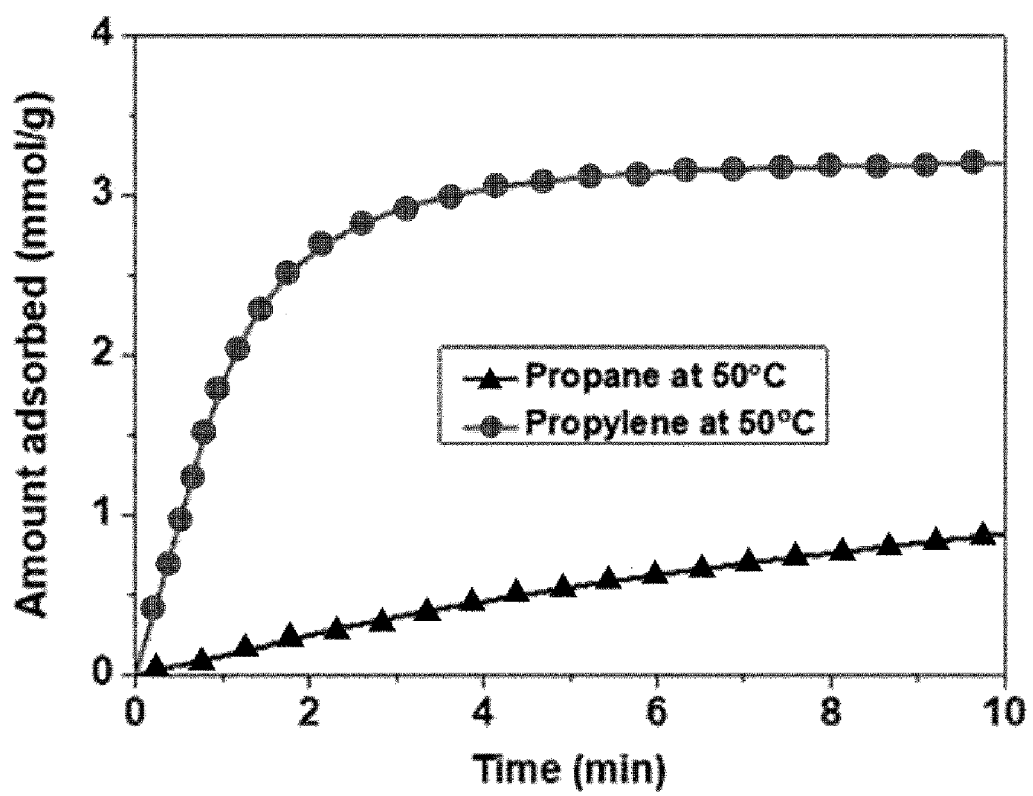

[FIG. 6]
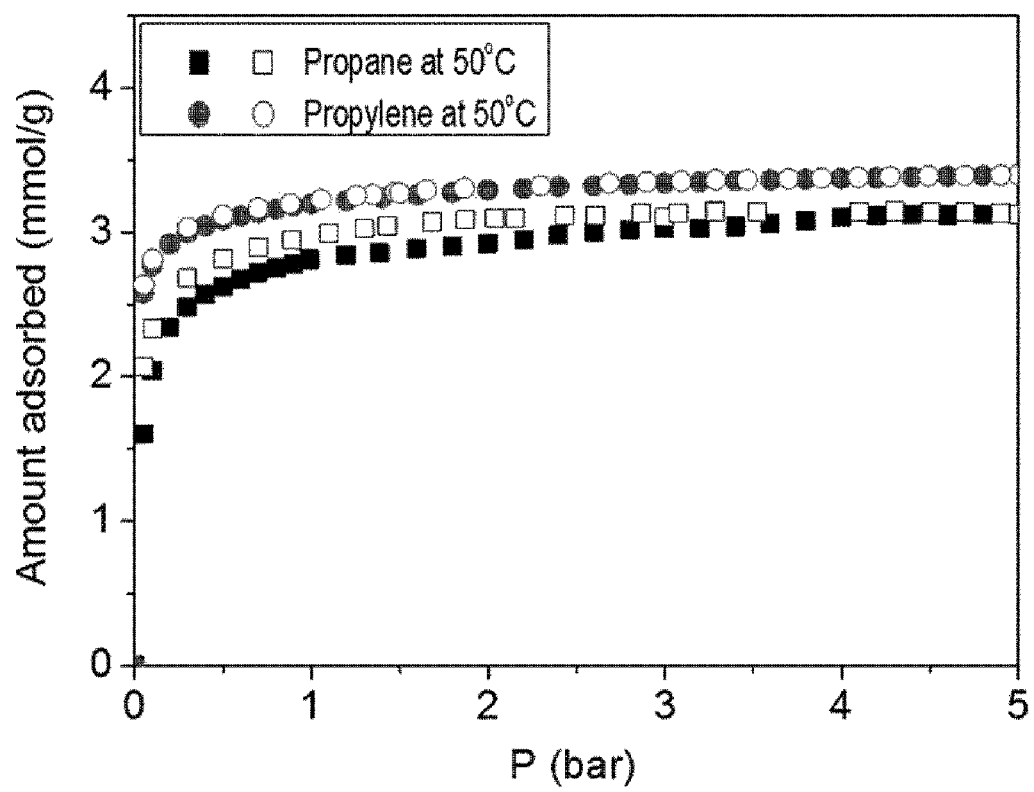

[FIG. 7]
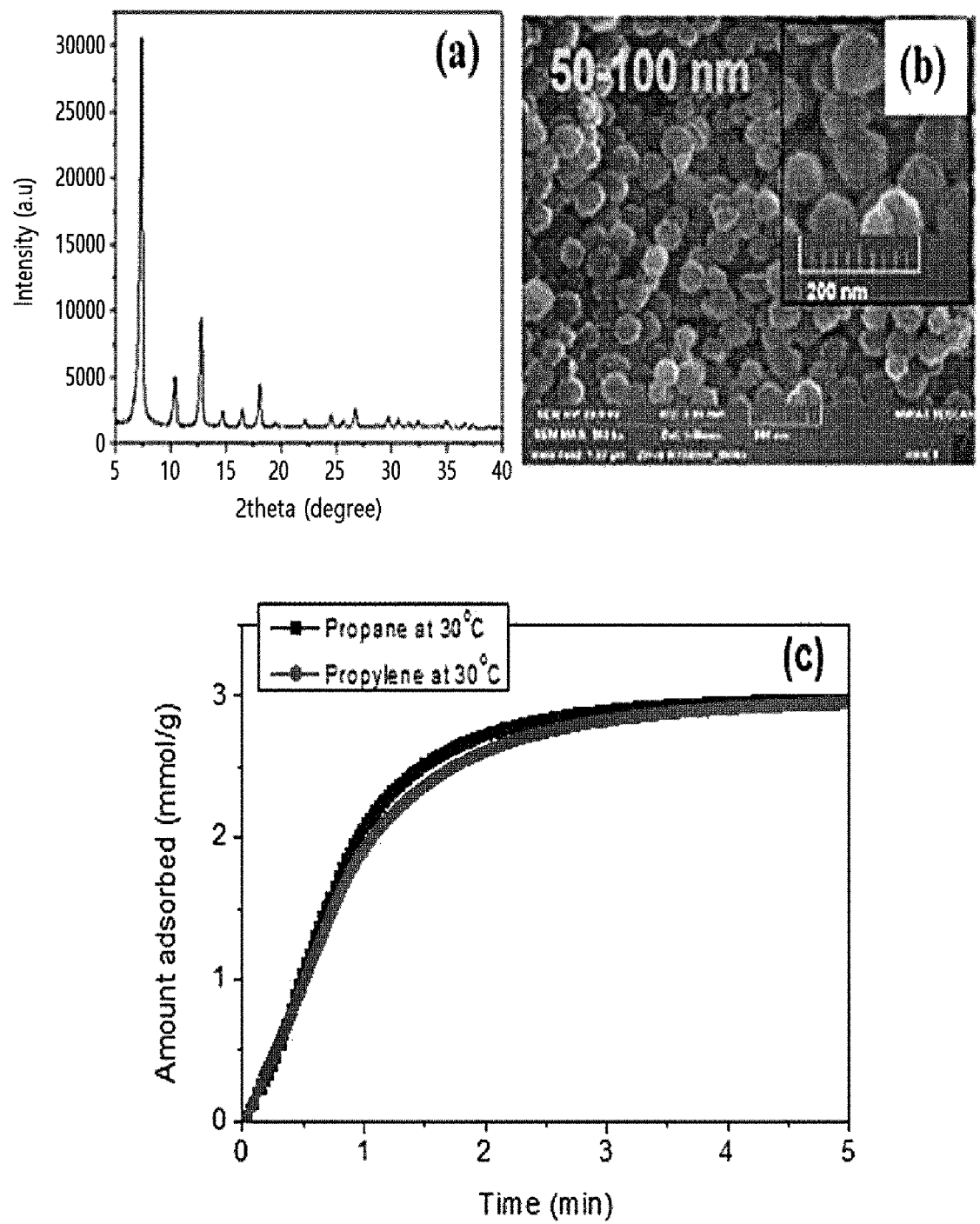

[FIG. 8]
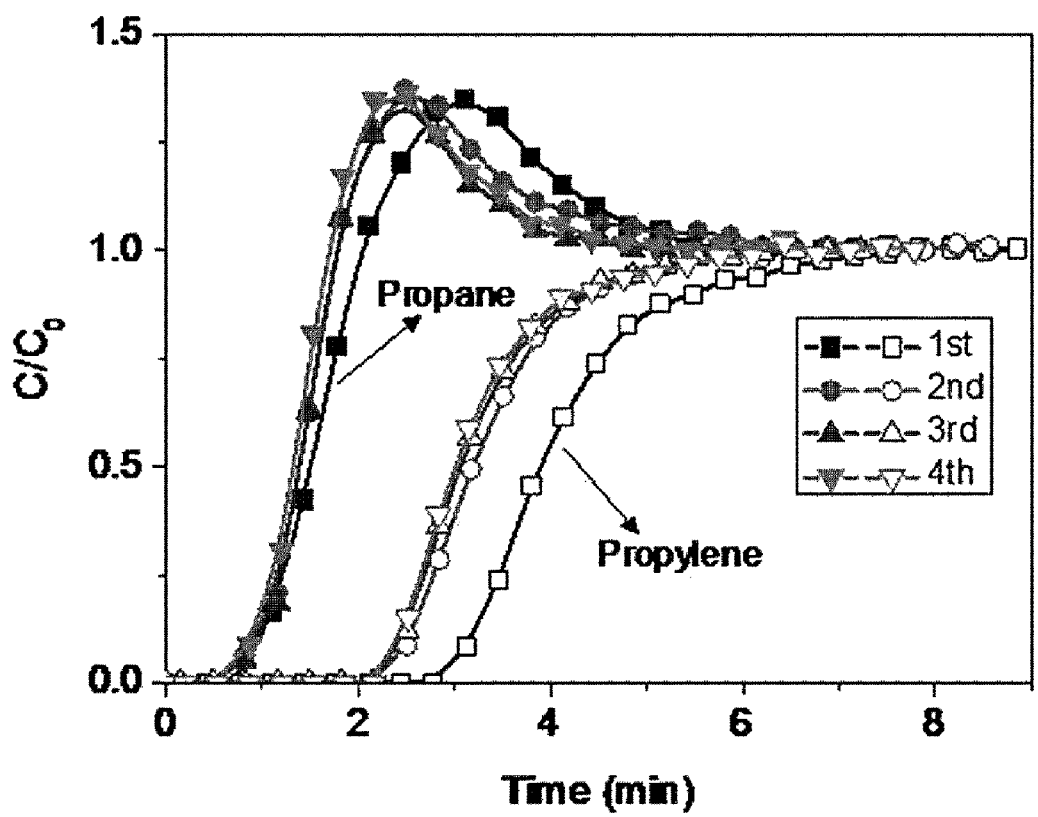

ORGANIC-INORGANIC HYBRID NANOPOROUS MATERIAL CONTAINING INTRAMOLECULAR ACID ANHYDRIDE FUNCTIONAL GROUP, COMPOSITION FOR ADSORPTION COMPRISING THE SAME, AND USE THEREOF FOR SEPARATION OF HYDROCARBON GAS MIXTURE

CROSS-REFERENCE TO RELATED APPLICATIONS

This application is the U.S. national phase of PCT Application No. PCT/KR2017/011461 filed on Oct. 17, 2017, which claims priority to KR Patent Application No. 10-2016-0134653 filed on Oct. 17, 2016, the disclosures of which are incorporated in their entirety by reference herein.

TECHNICAL FIELD

The present invention relates to an organic-inorganic hybrid nanoporous material, maintaining a nanoporous skeleton structure formed by coordination of an organic ligand containing an aromatic compound to a trivalent central metal ion, and further comprising an intramolecular acid anhydride functional group modified on the aromatic compound of the nanoporous skeleton structure, thereby exhibiting selectivity for olefins, and an adsorbent including the same. Specifically, the organic-inorganic hybrid nanoporous material of the present invention exhibits an excellent olefin-selective adsorption capacity through differences in adsorption equilibrium and adsorption rate, and thus can be usefully employed in the separation of $C_2$-$C_4$ hydrocarbons. Further, the olefins adsorbed to the organic-inorganic hybrid nanoporous material can be readily desorbed by purging of a non-condensable inert gas which is not easily liquefied by way of mild vacuum conditions or compression, and thus, the organic-inorganic hybrid nanoporous material can be used to prepare olefins by separation of $C_2$-$C_4$ hydrocarbon mixtures.

BACKGROUND ART

Currently, in the refining and petrochemical industries, olefin molecules having two to four carbon atoms, such as ethylene, propylene, butylene, etc., are among the most important raw materials for the production of synthetic resins such as polyethylene, polypropylene, polybutene, etc. and chemical products such as ethylbenzene, ethylene glycol, propylene glycol, etc., and are known as the most abundantly produced compounds in the petrochemical industry. In particular, ethylene and propylene monomers are produced worldwide with an annual output of 200 million tons in the petrochemical and gas chemical industries, and they are recognized as some of the most important chemical products sustaining modern industrial society. These olefin compounds are produced by various raw materials and processes such as thermal and catalytic cracking of naphtha, ethane cracking, propane dehydrogenation, cracking and dehydrogenation of shale gas ethane/propane, conversion of methanol to olefins, fluidized-bed catalytic cracking of heavy oil, etc. However, since ethylene, propylene, and butylene monomers having a purity of 99.5% or more must be prepared in order to be used as raw materials for polymer synthetic resins, in addition to a reaction process, a separation-purification process for obtaining high-purity olefin monomers from olefin and paraffin mixtures is very important. Despite low energy efficiency and excessive equipment costs, over the past several decades, the technology for separating olefin and paraffin mixtures has been driven by distillation processes. However, there has been a continuous demand for the development of an alternative process due to the excessive energy consumption of the distillation processes currently used. The currently used olefin separation-purification process, in which hydrocarbons are separated according to the number of carbon atoms, and olefins/paraffins having the same number of carbon atoms are isolated, is carried out by way of a multi-stage distillation method exploiting differences in the boiling point of each hydrocarbon. In the current production process of ethylene and propylene, the separation-purification process is problematic in that the boiling points of ethylene/ethane and propylene/propane molecules to be separated are very similar, such that a large amount of energy is consumed to separate these molecules by distillation, and the equipment cost is very high due to the large number of stages in the distillation column. In accordance with the Paris Agreement on Climate Change of 2015, a universal climate change agreement has been signed to mitigate global warming with global participation, and each country is making efforts to establish a new climate change framework after 2020. Under these circumstances, it has become an important issue to develop an economical new separation method, since the distillation process for separating olefins is a petrochemical process that generates large amounts of greenhouse gases due to excessive energy use. As one example, an adsorption separation process by way of an adsorbent which is selective to molecules of an olefin/paraffin, also known as a pressure swing adsorption (PSA) separation process, has been suggested as an efficient method. However, although the need for other separation processes has been raised during application of the distillation process over the last several decades, the most important reason that such an adsorption separation process has not been commercialized is that an adsorbent suitable for the separation of olefins, which is the core of the process, has not yet been developed.

To date, many porous adsorbents have been reported in patent documents and research papers as effective materials in the separation of olefins. Typical adsorbents have the following characteristics and disadvantages. As a first type of material, there has been proposed a porous adsorbent containing transition metal ions which are capable of selectively coordinating an olefin compound as a ligand, for example, monovalent silver ions and monovalent copper ions. Korean Patent No. 828137 discloses a method of producing an adsorbent in which silver nitrate ($AgNO_3$) is supported on a support in the form of pellets selected from alumino-silica gel, silica gel, and a mixture thereof. As an adsorbent used in such an adsorption separation process, U.S. Pat. Nos. 6,315,816 and 6,468,329 disclose an adsorbent prepared by supporting metal ions ($Ag^+$, $Cu^+$, etc.), which selectively adsorb olefins by forming a $\pi$ bond therewith, on a support having a large specific surface area (silica gel, alumina, alumino-silica gel, mesoporous materials, etc.). The metal ions are supported, for example, by impregnating a silver nitrate ($AgNO_3$) or copper (CuCl) solution on a support, followed by drying. Further, Korean Patent No. 787210 discloses a method for producing an adsorbent in which silver nitrate is supported on alumino-silica gel as an adsorbent suitable for separation of olefins/paraffins. However, the silver nitrate, being supported in the very small pores of the already small pores of the alumino-silica gel, has difficulty making contact with olefins or has a very slow mass transfer rate and thus may not be effective for adsorption. Thus, since the high-cost silver nitrate is wasted, the cost-competitiveness of high-cost adsorbents is not significantly improved. In addition, in the case of a support containing a metal ion, such as $Ag^+$, $Cu^+$, etc., the supported metal ion is easily reduced by the hydrocarbon mixture to be separated or by a reducing impurity gas contained in the mixture such as hydrogen, and thus, the separation performance is remarkably deteriorated. In addition, during the adsorption of olefin molecules, these adsorbents have a very high adsorption energy relative to paraffins and are strongly coordinated to the metal ions, and thereby exhibit a high adsorption selectivity for olefins over paraffins; however, there is a problem in that desorption becomes difficult.

As a second type of material, there has been proposed an olefin-selective adsorbent using a microporous zeolite which has been ion-exchanged with an alkali metal ion. French Patent No. 2,903,981, the inventors of which are researchers at the French Institute of Petroleum (IFP) and the University of Porto in Portugal, discloses a method for purifying propylene by selectively adsorbing propylene in the gas mixture of propane and propylene using zeolite 13X, which is selective for adsorption of propylene, as an adsorbent, then desorbing the propylene strongly absorbed to the pores using $C_4$ hydrocarbons, such as 1-butene or isobutane, as a desorbing agent, followed by isolating the desorbed propylene and $C_4$ hydrocarbons by a simulated moving bed (SMB) method. Although the zeolite 13X adsorbent is selective for propylene, it has a problem in that the adsorptive strength is too strong and a large amount of energy is consumed for desorption, such that it may be difficult to formulate an economical propylene/propane separation process.

As a third type of material, there has been proposed a molecular sieve-type zeolite adsorbent that can separate olefins and paraffins by exploiting the differences in molecular size between propylene and propane, or ethylene and ethane, as well as the differences in the diffusion rate for adsorption. According to the review articles of Ruthven and Reyes published in the United States (Micropor. Mesopor. Mater., 104: 59-66 (2007)), it is disclosed that zeolite molecular sieves having an octagonal pore shape fall within the category of the typical inorganic porous adsorbents that exhibit the differences in adsorption rate between propylene and propane, or ethylene and ethane. For example, these include molecular sieves such as zeolites 4A, 5A, Si-CHA, DD3R, SAPO-34, etc., and they have elliptically shaped pores with a size in the range of 3.65 Å×4.6 Å. In addition, Olson et al. (J. Phys. Chem. B, 108: 11044-11048 (2004)) discloses an ITQ-12 material, which is another octagonal silica zeolite, as an adsorbent for separation of propylene/propane, and also shows that at 30° C., the adsorption rate of propylene is more than 100 times faster than that of propane. Since these molecular sieve-type zeolite adsorbents have similar adsorption amounts for propylene and propane at typical adsorption temperature and pressure, the separation must be carried out according to differences in the adsorption rate. Also, due to the large difference in the adsorption rate, instead of selectively adsorbing olefin molecules such as propylene or ethylene, some olefin molecules may block the pore openings or may not be easily desorbed after accumulating in the narrow pores. Thus, there is a disadvantage in that it is difficult to implement the typical commercialized adsorption separation process of PSA separation technology, wherein these molecules are purified by repeating the adsorption process at high pressure and the desorption process at low pressure under the same temperature conditions.

In recent years, in order to overcome the disadvantages of inorganic porous adsorbents, organic-inorganic hybrid nanoporous materials, i.e., organic-inorganic skeleton compounds, also known as metal-organic frameworks (MOF), have been applied to many studies related to olefin/paraffin adsorption separation. In this regard, as a fourth type of material for olefin/paraffin adsorption separation, there has been proposed a porous hybrid material with a high adsorption rate of propylene relative to propane, similar to the third type of material above. Jing Li et al., published in the United States (J. Am. Chem. Soc., 131: 10368-10369 (2009)), reports that a hybrid nanoporous material having a zeolite-type structure, i.e., a zeolitic imidazolate framework-8 (ZIF-8) in which a divalent Zn(II) ion is bound to a 2-methyl-imidazole ligand compound, has adsorption rate selectivity for propylene. The selectivity according to the diffusion rate coefficient of propylene relative to propane for this adsorbent at 30° C. was found to be as high as 125. However, in this study, the ZIF-8 adsorbent was used, having a large crystal size of 100 μm or more, and while such a large crystal size can be obtained in a laboratory-scale synthesis, it cannot be easily obtained in a large-scale synthesis to allow for commercial application. Moreover, when a ZIF-8 adsorbent having a crystal size of 10 μm or less is used, the differences in the adsorption rate between propylene and propane are not very large, and thus these ZIF-8 adsorbents are not suitable for adsorption separation of propylene and propane.

As a fifth type of material for olefin/paraffin adsorption separation, an organic-inorganic hybrid nanoporous material may be included which contains metal ions with an unsaturated coordination site. Until now, hybrid nanoporous materials such as Cu-BTC (Chem. Eng. J., 167: 1-12 (2011)), MIL-100(Fe) (Angew. Chem., Int. Ed., 49: 4958-4961 (2010)), Fe(II)-MOF-74 (Science, 335: 1606-1610 (2012)), etc. have been known to have a coordinatively unsaturated metal site, thereby increasing the selectivity of adsorption by coordinating π electron-bearing propylene. However, since these adsorbents are strongly adsorbed in the pores as in the case of the first type of adsorbents, after completion of the adsorption, it is necessary to increase the temperature or to apply a high vacuum condition during desorption. Thus, there is a problem in that it is difficult to apply these adsorbents as adsorbents for the PSA separation technology.

DISCLOSURE

Technical Problem

The object of the present invention is, with respect to hydrocarbons having 2 to 4 carbon atoms, to provide a hybrid nanoporous material having a relatively high adsorption amount of olefins compared to paraffins, exhibiting a rapid adsorption rate of olefins compared to paraffins under the same pressure, and having a feature in that the adsorbed olefins are easily desorbed under a mild condition, and a method for improving olefin/paraffin separation efficiency using an adsorbent including the same.

Technical Solution

A first aspect of the present invention is to provide an organic-inorganic hybrid nanoporous material, maintaining a nanoporous skeleton structure formed by coordination of an organic ligand containing an aromatic compound to a trivalent central metal ion, and further comprising an intra-molecular acid anhydride functional group modified on the aromatic compound of the nanoporous skeleton structure.

A second aspect of the present invention is to provide a composition for adsorption, including the organic-inorganic hybrid nanoporous material according to the first aspect.

A third aspect of the present invention is to provide an adsorbent for separating $C_2$-$C_4$ hydrocarbons composed of a compound, in which an independent COOH functional group which is not coordinated to a metal ion in a benzenetricarboxylic acid organic ligand coordinated to a trivalent central metal ion is present, and which contains the composition of Chemical Formula 2, or a hydrate or solvate thereof:

$$A_xB_yC_z \quad \text{[Chemical Formula 2]}$$

$A=\{M_4(\mu_2\text{-OH})_4[(CO_2)_2C_6H_3COOH]_4\}$
$B=\{M_4(\mu_2\text{-OH})_4[C_6H_4(CO_2)_2]_4\}$
$C=\{M_4(\mu_2\text{-O})_d(\mu_2\text{-OH})_e[(CO_2)C_6H_3(CO)_2O]_4\}$ in Chemical Formula 2, M=a trivalent metal ion; x+y+z=1; x>0; y≥0; z≥0 (with the proviso that y=z=0 is excluded); 0≤d≤4; 0≤e≤4; and d, e, x, y, and z are rational numbers.

A fourth aspect of the present invention is to provide an apparatus for adsorption separation of $C_{2\text{-}4}$ hydrocarbons, including the organic-inorganic hybrid nanoporous material according to the first aspect or the adsorbent for separating $C_2$-$C_4$ hydrocarbons according to the third aspect.

A fifth aspect of the present invention is to provide a method for separating olefins and paraffins having the same number of carbon atoms, including:
contacting a mixture of olefins and paraffins having the same number of carbon atoms in $C_{2\text{-}4}$ hydrocarbons with the organic-inorganic hybrid nanoporous material according to the first aspect or the adsorbent for separating $C_2$-$C_4$ hydrocarbons according to the third aspect,
wherein the adsorption-desorption temperature is from −30° C. to 150° C. and the adsorption-desorption pressure is from 0.1 bar to 35 bar.

A sixth aspect of the present invention is to provide a method for separating hydrocarbons having a different number of carbon atoms, including:
contacting a mixture containing $C_{1\text{-}4}$ hydrocarbons having a different number of carbon atoms with the organic-inorganic hybrid nanoporous material according to the first aspect or the adsorbent for separating $C_2$-$C_4$ hydrocarbons according to the third aspect,
wherein the adsorption-desorption temperature is from −30° C. to 150° C. and the adsorption-desorption pressure is from 0.1 bar to 35 bar.

A seventh aspect of the present invention is to provide a method for separating olefin and paraffin gases from a mixed hydrocarbon gas, including:
contacting a mixed $C_{1\text{-}4}$ hydrocarbon gas with the organic-inorganic hybrid nanoporous material according to the first aspect or the adsorbent for separating $C_2$-$C_4$ hydrocarbons according to the third aspect,
wherein the adsorption-desorption temperature is from −30° C. to 150° C. and the adsorption-desorption pressure is from 0.1 bar to 35 bar.

An eighth aspect of the present invention is to provide a method for preparing $C_{2\text{-}4}$ olefins, including:
a first step of adsorbing olefins in $C_{2\text{-}4}$ hydrocarbons to an adsorbent including the organic-inorganic hybrid nanoporous material according to the first aspect, or the adsorbent for separating $C_2$-$C_4$ hydrocarbons according to the third aspect; and
a second step of purging the adsorbent to which $C_{2\text{-}4}$ olefins are adsorbed with an inert gas.

A ninth aspect of the present invention is to provide a method for preparing the organic-inorganic hybrid nanoporous material according to the first aspect, including:
a first step of preparing a mixed solution of a trivalent metal ion-containing metal precursor, an organic ligand containing an aromatic compound substituted with two or more carboxylic acid functional groups, and a nitrogen-containing basic compound in a reaction vessel;
a second step of placing the reaction vessel in a pressure reactor and allowing it to react at 100° C. to 200° C. for 10 to 20 hours; and
a third step of heat-treating the solid product obtained from the previous step at a temperature of 350° C. to 500° C.

Advantageous Effects

The novel organic-inorganic hybrid nanoporous material of the present invention having an intramolecular acid anhydride functional group is capable of selectively adsorbing olefins over paraffins having the same number of carbon atoms due to a high equilibrium adsorption amount and a rapid diffusion rate with respect to a $C_{2\text{-}4}$ hydrocarbon compound, thereby exhibiting a feature in olefin/paraffin rate separation. Therefore, since the organic-inorganic hybrid nanoporous material of the present invention has a greater adsorption-desorption working capacity for olefins than an adsorbent only capable of rate separation, the olefin/paraffin separation can be carried out effectively. In addition, the adsorbed olefin can be easily desorbed and recovered under a mild vacuum condition or by purging with an inert gas, and thus this can be utilized in the production of olefins.

BRIEF DESCRIPTION OF DRAWINGS

FIG. 1 is a diagram showing the result of X-ray diffraction analysis of Al-TMA(NP) and MOF-Anhydride material according to Preparation Example 1 of the present invention. In this spectrum, (a) shows the hydrated Al-TMA(NP), (b) shows the hydrated MOF-Anhydride, and (c) shows the X-ray diffraction spectrum of MOF-Anhydride dried at 200° C.

FIG. 2 is a diagram showing the in situ infrared spectroscopy spectrum of MOF-Anhydride vacuum-dried at 200° C. Herein, the spectrum in the range of 3500 $cm^{-1}$ to 3800 $cm^{-1}$ contains the OH stretching vibration peaks of the OH functional groups in the MOF-Anhydride structure, and the spectrum in the range of 1750 $cm^{-1}$ to 1950 $cm^{-1}$ contains the C=O stretching vibration peaks of the acid anhydride functional groups formed in the aromatic rings of the MOF-Anhydride structure.

FIG. 3 is a thermogravimetric analysis graph showing the weight loss with increasing temperature of the hydrated Al-TMA(NP) and the hydrated MOF-Anhydride material. In this graph, (a) shows the thermogravimetric analysis graph of the hydrated Al-TMA(NP), and (b) shows the thermogravimetric analysis graph of the hydrated MOF-Anhydride. At this time, the analysis conditions were as follows: nitrogen with a velocity of 50 cc/min was used as a transfer gas, and the temperature was increased at a rate of 5° C. per minute.

FIG. 4 is a graph showing the adsorption-desorption isotherms of propane and propylene at 50° C. in the dried MOF-Anhydride material (filled symbol: adsorption, blank symbol: desorption).

FIG. 5 is a graph showing the adsorption rate curves of propane and propylene according to the time at an adsorption temperature of 50° C. and an adsorption pressure of 1 atm in the dried MOF-Anhydride material (filled triangle: propane, filled circle: propylene).

FIG. 6 is a graph showing the adsorption-desorption isotherms of propane and propylene in the dried zeolite 13X adsorbent at 50° C.

FIG. 7 shows a graph (a) illustrating the X-ray diffraction pattern of ZIF-8 adsorbent having a particle size of 1 µm or less, a scanning electron microscopic image (b), and a graph comparing the single component adsorption rate of propylene/propane at 30° C.

FIG. 8 is a graph showing the adsorption breakthrough curves of propane and propylene in the dried MOF-Anhydride material at 5 atm and 70° C., and the adsorption breakthrough curves when the process was repeated using nitrogen as a transfer gas (filled symbol: propane, blank symbol: propylene). At this time, the experimental conditions were as follows: the MOF-Anhydride material was filled into an adsorption breakthrough column in the form of a spherical body having a diameter of 1 mm to 2 mm, and a propane/propylene mixed gas having a molar composition ratio of 60% to 40% was supplied at a flow rate of 50 cc/min to carry out the breakthrough experiment. After the first adsorption breakthrough experiment, the propylene/propane adsorbed to the adsorbent was desorbed by supplying a nitrogen transfer gas with a flow rate of 45 cc/min at a pressure of 5 atm and a temperature of 70° C. for 30 minutes. Subsequently, a second adsorption breakthrough experiment was carried out by supplying a propane/propylene mixed gas having a molar composition ratio of 60% to 40% at a flow rate of 50 cc/min to obtain third and fourth adsorption breakthrough curves under the same desorption and re-adsorption conditions.

DETAILED DESCRIPTION OF EMBODIMENTS

Gas separation is largely carried out by utilizing the differences in two characteristics of the thermodynamic adsorption equilibrium and adsorption rate between adsorbents and adsorbate gases. In this case, the interaction and affinity between the adsorbents and the adsorbate gas molecules plays an important role in the gas separation, but the diffusion rate at which the molecules pass through the pores also plays a very important role.

Conventional adsorbents generally exhibit separation performance by either equilibrium separation, using the thermodynamic adsorption property between the adsorbents and the adsorbate molecules, or rate separation, using the differences in the adsorption rate.

When the rate separation occurs in rate-selective adsorbents, equilibrium separation performance is hardly exhibited, while the separation performance is exhibited due to the differences occurring in the diffusion rate of the gases in the pores of the adsorbent, which has a pore size that allows the differences in the size of the adsorbate gas molecules to be distinguished. Thus, in general, the rate-selective adsorbent utilizes the differences in the rate of the adsorbates to be separated, and in most cases, the differences in the adsorption amount between the molecules to be separated are significant.

Further, in the case of equilibrium-selective adsorbents, the differences in the interaction between the adsorbent and adsorbate molecules are the main driving force for generating differences in the thermodynamic equilibrium of the gas separation. In this case, the size of the adsorbent pore hardly leads to any difference in the diffusion rate between the adsorbate molecules. Thus, it is common in the prior art to select an adsorbent such that separation is performed only by either the equilibrium separation, using the thermodynamic adsorption property between the adsorbent and the adsorbate molecules, or the rate separation, using the differences in the adsorption rate. For example, in the case of X-type zeolite adsorbents exchanged with alkali metal ions, lithium ion-containing Li—X zeolite has a strong interaction with nitrogen molecules, such that the equilibrium adsorption amount of nitrogen molecules is larger than the equilibrium adsorption amount of oxygen molecules, and thus it is widely used as an equilibrium-selective adsorbent for separating nitrogen and oxygen in the air. Further, carbon molecular sieves (CMS) have a limited pore size of about 3 Å to 5 Å, and thus are utilized in the adsorption separation process using the concept of rate separation due to the differences in the rate at which the adsorbate molecules pass through the pores. Recently, Jing Li et al. disclosed in U.S. Pat. No. 8,796,462 that the hybrid nanoporous material ZIF-8, which forms a three-dimensional skeleton compound in the form of a central metal iron coordinately linked to imidazole-based ligands, is an adsorbent known to have adsorption selectivity for propylene over propane, and is known as an rate-selective adsorbent for propylene because when propylene and propane are adsorbed, the diffusion rate of propylene in the pores is larger than the diffusion rate of propane. However, since there is almost no difference in the equilibrium adsorption amount between propylene and propane under the same adsorption conditions, there is a limitation in effectively separating and purifying propylene and propane by using only the differences in the adsorption rate when applying the PSA process. In the case of the ZIF-8 adsorbent, the diffusion rate in the pores greatly depends on the particle size of the adsorbent in the adsorption of propylene and propane. In order to obtain a difference in the adsorption rate applicable to the adsorption separation of propylene/propane, an adsorbent having a size of 100 µm or more is required. If the particle size is less than 1 µm, there is almost no difference in the adsorption rate between propylene and propane (Comparative Example 2). Since it is difficult in actual practice to synthesize a porous adsorbent having a particle size of 100 µm or more in large quantities, such particle size dependency can be a major limitation in use as a commercial adsorbent.

The present inventors have made extensive efforts to design a hybrid nanoporous material adsorbent having a large working capacity between the adsorbing and desorbing conditions, while exhibiting a difference in the equilibrium adsorption amount between olefins and paraffins, allowing for easy desorption of olefins and paraffins, and have discovered a nanoporous material of a novel structure having a intramolecular acid anhydride functional group formed on an organic ligand of a skeleton of the organic-inorganic hybrid nanoporous material (for example, MOF), and have also found that the nanoporous material can serve as a novel adsorbent for separating olefins and paraffins based on adsorption equilibrium and adsorption rate, while exhibiting a difference in the adsorption rate between olefins and paraffins, together with the above-described characteristics. For example, when the porous coordination polymer compound formed from the trivalent metal ion and 1,2,4-benzenetricarboxylic acid ligand selected in the present invention, that is, the organic-inorganic hybrid nanoporous material, is primarily synthesized in an aqueous solution, obtained in a solid state, heat-treated, hydrated under a condition in which the ambient environment is well controlled, and dried, intramolecular acid anhydride functional groups, which are not the intermolecular acid anhydride functional groups generally predicted, are formed in the aromatic rings of the organic ligand coordinately linked to the central metal during the formation of the skeleton of the organic-inorganic hybrid nanoporous material, thereby providing a nanoporous material (hereinafter referred to as MOF-Anhydride for convenience), which is a compound containing the composition of $\{[C_6H_3(CO_2)C_2O_3]_a M_4(O)_b (OH)_c\}$ (wherein a, b, and c are each independently a rational number from 0 to 4) in the Chemical Formula of the skeleton structure, or a hydrate or a solvate thereof. The organic-inorganic hybrid nanoporous material used in the present invention can be abbreviated as MOF-Anhydride. Herein, M, the central metal, can be various trivalent metal ions. Also, the porous coordination polymer solid compound used for the preparation of MOF-Anhydride in the present invention can be obtained from a trivalent metal ion salt and a 1,2,4-benzenetricarboxylic acid ligand as precursors. For example, in the case of an aluminum-based porous coordination polymer solid compound, an aluminum chloride hydrate, which is conventionally used as an aluminum precursor in the synthesis, may damage the metal reactor due to the corrosion of hydrochloric acid generated during the synthesis under a high-temperature pressurized condition, leading to perforation. Thus, the compound can be synthesized by replacement with aluminum sulfate or another aluminum compound and adding a certain amount of a nitrogen-containing basic additive. When such a synthesis condition is adopted, the synthesis temperature of the porous coordination polymer solid compound can be lowered and the yield can be greatly improved, thereby effectively preparing a MOF-Anhydride material. The present inventors have found that an adsorbent including the thus-prepared MOF-Anhydride nanoporous material is suitable for the separation of saturated or unsaturated $C_{2-4}$ hydrocarbon compounds. In particular, they also have found that the MOF-Anhydride nanoporous material has a relatively high equilibrium adsorption amount and a high adsorption rate of olefins in mixtures of olefins and paraffins having the same number of carbon atoms, and is thus suitable for the separation of olefins. In addition, the adsorbed olefins can be easily desorbed under a low vacuum or by purging with an inert gas, and thus, this is also suitable for the recovery of olefins. The present invention is based on these findings.

The present invention may provide an organic-inorganic hybrid nanoporous material, maintaining a nanoporous skeleton structure formed by coordination of an organic ligand containing an aromatic compound to a trivalent central metal ion, and further comprising an intramolecular acid anhydride functional group modified on the aromatic compound of the nanoporous skeleton structure.

Specifically, the skeleton structure of the organic-inorganic hybrid nanoporous material may be a compound containing a composition represented by the following Chemical Formula 1:

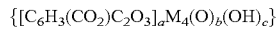  [Chemical Formula 1]

in Chemical Formula 1, M is a trivalent metal ion, and a, b, and c are each independently a rational number from 0 to 4.

Herein, the compound may be in the form of a hydrate or a solvate which includes the composition of Chemical Formula 1 and in which 20 or fewer water molecules or organic solvent molecules are bound per unit molecule. For example, when the compound is synthesized in an aqueous solution phase using water as a solvent, it can be synthesized in the form of a hydrate, or when it is synthesized in an organic solvent phase instead of an aqueous solution, or when an organic solvent is used in the activation process after synthesis, it can be obtained in the form of a solvate in which the organic solvent molecules are bound instead of water molecules.

For example, M, which is a trivalent metal, may be $Al^{3+}$, $Ga^{3+}$, $In^{3+}$, $Fe^{3+}$, $Cr^{3+}$, $V^{3+}$, or a combination thereof. Specifically, the M may be $Al^{3+}$ or at least partly include $Al^{3+}$, but is not limited thereto.

In a specific embodiment of the present invention, it has been confirmed that the synthesized nanoporous material is composed of the compound represented by Chemical Formula 1 containing an intramolecular acidic anhydride functional group through X-ray structure analysis and in situ IR analysis of the newly synthesized nanoporous material.

The present invention provides a method for preparing an organic-inorganic hybrid nanoporous material, maintaining a nanoporous skeleton structure formed by coordination of an organic ligand containing an aromatic compound to a trivalent central metal ion, and further comprising an intramolecular acid anhydride functional group modified on the aromatic compound of the nanoporous skeleton structure. The organic-inorganic hybrid nanoporous material according to the present invention may be prepared by the method including:

a first step of preparing a mixed solution of a trivalent metal ion-containing metal precursor, an organic ligand containing an aromatic compound substituted with two or more carboxylic acid functional groups, and a nitrogen-containing basic compound in a reaction vessel;

a second step of placing the reaction vessel in a pressure reactor and allowing it to react at 100° C. to 200° C. for 10 to 20 hours; and a third step of heat treating the solid product obtained from the previous step at a temperature of 350° C. to 500° C.

For example, as the nitrogen-containing basic compound, N,N-dimethylformamide (DMF), N,N-dimethylacetamide (DMAC), N-methylpyrrolidone (NMP), urea, or $NH_4OH$ may be used alone or in a combination of two or more thereof, but is not limited thereto.

As the organic ligand, 1,2,4-benzenetricarboxylic acid, an ester, an anhydride, or a salt derivative thereof may be used alone or in a combination of two or more thereof, but is not limited thereto.

In the preparation method of the present invention, the trivalent metal ion-containing metal precursor and the organic ligand may be used in a ratio of 0.5 mol to 1.5 mol of the metal ion relative to 1 mol of the organic ligand.

Further, the preparation method of the present invention may further include a step of separating and purifying the solid product obtained after the second step. For example, after completion of the reaction of the second step, remaining unreacted trivalent metal ions, the corresponding anions thereof, and the organic ligand coexist in the reactor in addition to the solid product, and thus, a step of dispersing the mixture in distilled water and ethanol and filtering with a vacuum filter, followed by recovering the solid product and washing, and/or a step of drying may be additionally carried out.

Meanwhile, in the preparation method of the present invention, the third step may be carried out for 4 to 12 hours under vacuum or an inert gas flow at a pressure of $10^{-4}$ Torr or less, but is not limited thereto.

Further, after the third step, a step of allowing the obtained nanoporous material to stand in the air may be further included. At this time, the nanoporous material to be recovered may be a hydrated or solvated nanoporous material to which water used as a solvent or an organic solvent is coordinated.

Accordingly, the nanoporous material may be provided in a dried state in which the coordinated water or other organic solvent molecules are removed by inclusion of an additional drying step, but is not limited thereto.

In addition, the present invention may provide a composition for adsorption, including the organic-inorganic hybrid nanoporous material.

The composition for adsorption of the present invention may be used for separation of $C_{1-4}$ hydrocarbons according to the number of carbon atoms or for separation of olefins and paraffins having the same number of carbon atoms in $C_{2-4}$ hydrocarbons.

Further, the adsorbent, which is favorably used for adsorption equilibrium and rate separation of olefins vs. paraffins, is placed into a column or an adsorption vessel and subjected to heat treatment prior to use in the separation for the purpose of pretreatment. In this regard, the present inventors have found that the form of the adsorbent exhibiting selectivity for the adsorption separation of $C_2$-$C_4$ hydrocarbons is composed of the sum of the following three-component chemical composition $A_xB_yC_z$ (Chemical Formula 2):

$A=\{M_4(\mu_2\text{-OH})_4[(CO_2)_2C_6H_3COOH]_4\}$
$B=\{M_4(\mu_2\text{-OH})_4[C_6H_4(CO_2)_2]_4\}$
$C=\{M_4(\mu_2\text{-O})_d(\mu_2\text{-OH})_e[(CO_2)C_6H_3(CO)_2O]_4\}$ in Chemical Formula 2, M=a trivalent metal ion; $x+y+z=1$; $x>0$; $y\geq 0$; $z\geq 0$ (with the proviso that $y=z=0$ is excluded); $0\leq d\leq 4$; $0\leq e\leq 4$; and d, e, x, y, and z are rational numbers.

Specifically, M is as defined above.

The hydrates and solvates of the present invention are as defined above. In the present invention, each of the compositions of Chemical Formula 2 may be independently in the form of an anhydride, a hydrate, or a solvate. For example, it may be in the form of an anhydride formed by elimination of all water molecules or organic solvent molecules through a heat treatment process, or in the form of a hydrate or solvate from which only a few molecules are eliminated.

In the adsorbent compound, A is a chemical composition formed during drying of the synthesized adsorbent.

B is a chemical composition formed upon decomposition of COOH groups by decarboxylation during drying and heat treatment of the adsorbent at a temperature of 200° C. or higher.

C is a chemical composition in which an anhydride is formed by dehydration condensation between adjacent COOH groups during drying and heat treatment of the adsorbent at a temperature of 100° C. or higher.

The changes in the heat treatment temperature and the changes in the structure of the adsorbent during adsorption and desorption of hydrocarbons at the adsorption temperature in the case where an aluminum ion was contained in the adsorbent composition were analyzed by X-ray diffraction patterns, and as a result, the pore size of the organic-inorganic hybrid nanoporous material represented by Chemical Formula 2 according to the present invention gradually increases as the adsorption pressure increases, starting from a relatively small pore structure before adsorption. In addition, the unit lattice and pore size of the organic-inorganic hybrid nanoporous material are subjected to change and increase during the adsorption process of olefins and paraffins, and the total adsorption amount of olefins and paraffins increases as the size of the unit lattice increases. When the adsorbed molecules are desorbed, the unit lattice becomes relatively small. That is, the organic-inorganic hybrid nanoporous material according to the present invention can exhibit skeleton elasticity during adsorption and desorption of $C_2$-$C_4$ hydrocarbon adsorbates. The skeleton elasticity can be altered according to the temperature and pressure under the adsorption and desorption conditions of the $C_2$-$C_4$ hydrocarbons. Also, when the adsorbate molecules are adsorbed in a gas phase, the change in the size of the unit lattice in the adsorbent is relatively small compared to when they are adsorbed in a liquid phase. However, the elasticity ratio between when the unit lattice is smallest and when the unit lattice is expanded to its largest may generally be in the range of 100% to 150%.

In the case of propylene/propane adsorption, the ABC chemical composition is optimized when the pretreatment temperature of the organic-inorganic hybrid nanoporous material represented by Chemical Formula 2 is 100° C. or higher, and the pore size is changed so that olefins can pass through the pores quickly and easily. In contrast, propane, which is slightly larger in molecular size than propylene, has a slower adsorption rate, thereby increasing the difference in the rate between propane and propylene. Since the interaction between olefins and paraffins in the pores is more desirable for olefins in the optimized composition, the adsorption amount of olefins is higher than that of paraffins.

In the ABC chemical composition, each of A, B, and C is present in one skeleton of the nanoporous material, and the pores are positioned adjacent to one another and are bound to one another, and thus, an interrelated action occurs each time the pores are expanded or contracted during adsorption and desorption of olefin and paraffin molecules.

Therefore, in the adsorption process of olefin and paraffin hydrocarbon molecules having 2 to 4 carbon atoms, the hybrid nanoporous material according to the present invention accelerates the diffusion rate of the olefin molecules in the pores via the action of the independent functional group and the nanoporous skeleton, causing a difference in the adsorption rate, and also exhibits a feature in that the olefin and paraffin molecules adsorbed in the nanoporous material are easily desorbed during the desorption process, and thus, the olefin molecules can be selectively adsorbed, separated, and purified from an olefin-paraffin gas mixture using this material.

Accordingly, in the present invention, with respect to $C_2$-$C_4$ hydrocarbons along adsorption isotherms, a new hybrid nanoporous material has been discovered which has a higher adsorption amount of olefins relative to paraffins, and which exhibits a higher adsorption rate of olefins relative to paraffins under the same pressure, and has been applied as an adsorbent for the olefin/paraffin separation process.

Further, it has been confirmed that since the adsorbent developed herein has a feature in that during the desorption process, the adsorbed olefins are easily desorbed under atmospheric pressure or a mild condition of about 0.3 atm or by an inert gas such as $N_2$, He, Ar, etc. at the same pressure as the adsorption, the adsorbent is effective for constructing a highly efficient olefin/paraffin adsorption separation technology.

The organic-inorganic hybrid nanoporous material which can be used as an adsorbent for equilibrium adsorption and rate adsorption according to the present invention enables the separation according to the adsorption rate in the $C_2$-$C_4$ hydrocarbons regardless of the type of paraffin/olefin, and can be preferably used to separate $C_2$-$C_4$ hydrocarbons, and more preferably $C_3$ hydrocarbons (propane/propylene) or $C_2$ hydrocarbons (ethane/ethylene). In addition, while olefin molecules are more desirable compared to paraffin molecules in terms of equilibrium separation, the rate separation, which is driven by the differences in the adsorption rate, can also be carried out, and thus there is an advantage in that the conventional rate separation's problem of separation efficiency due to a small adsorption amount can be greatly improved.

The organic-inorganic hybrid nanoporous material which can be used as an adsorbent for equilibrium adsorption and rate adsorption according to the present invention may control the differences in the adsorption rate between paraffins/olefins by controlling the adsorption temperature.

When the adsorbent according to the present invention is used to separate $C_2$-$C_4$ hydrocarbons, the adsorption-desorption temperature may be from −30° C. to 150° C., and the adsorption-desorption pressure may be from 0.1 bar to 35 bar.

Further, an apparatus for adsorption separation of $C_{2-4}$ hydrocarbons including the organic-inorganic hybrid nanoporous material of the present invention may be constructed.

For example, the adsorption separation apparatus may be equipped with an adsorption apparatus including the organic-inorganic hybrid nanoporous material of the present invention as an adsorbent for adsorbing olefins. The adsorption apparatus may be a fixed bed column, a fluidized bed column, or a moving bed column filled with the organic-inorganic hybrid nanoporous material of the present invention as an adsorbent.

The adsorption separation apparatus of the present invention is based on the fact that the organic-inorganic hybrid nanoporous material of the present invention exhibits different adsorption for olefins and paraffins having the same number of carbon atoms in $C_{2-4}$ hydrocarbons and/or for hydrocarbons having a different number of carbon atoms. Thus, the adsorption separation apparatus of the present invention may be used for separation of olefins and paraffins having the same number of carbon atoms, separation of hydrocarbons having a different number of carbon atoms, and separation of olefin and paraffin gases from a mixed hydrocarbon gas.

Furthermore, the adsorption separation apparatus may further include means for desorbing the olefins adsorbed to the organic-inorganic hybrid nanoporous material to recover the olefins.

The adsorption separation apparatus may be driven by a pressure swing adsorption-desorption method, a pressure-vacuum swing adsorption-desorption method, a temperature swing adsorption-desorption method, an adsorption-desorption method by purging with an inert gas, or a combination thereof, but the adsorption-desorption methods applicable to the apparatus of the present invention are not limited thereto.

The adsorption process is a process by which energy can be saved compared to other separation processes and can be largely classified into a pressure swing adsorption process and a temperature swing adsorption process depending on the regeneration method. Adsorption is a phenomenon in which gaseous components in a gas phase are physically or chemically bound to a porous solid surface. Typically, the adsorption rate and adsorption amount increase as the reaction temperature decreases. Desorption of the adsorbed material may be carried out by using pressure or increasing the temperature, or by using a desorbent.

Meanwhile, pressure swing adsorption (PSA) is a process technology by which adsorbates are adsorbed and removed under high pressure in order to purify a specific gas from a mixed gas with high purity, and the pressure is lowered when the adsorbates are desorbed and recovered. Pressure swing is a phenomenon in which the pressure is periodically converted from high pressure to low pressure. Meanwhile, vacuum swing adsorption (VSA), by which desorption is carried out under vacuum conditions, falls within the category of PSA.

In PSA, desorption may be induced by lowering the partial pressure of the adsorbates in the mixed gas, or the partial pressure may be lowered by lowering the pressure of the mixed gas itself.

That is, when a gaseous raw material is passed through an adsorption column filled with a porous adsorbent under high pressure, the components having high selectivity are first adsorbed, and the components having low selectivity are discharged from the adsorption column. The pressure in the adsorption column is lowered to remove the adsorbed components, thereby recovering the adsorbed components, and the column is washed with some of the high-pressure products. The products can be continuously obtained by repeating this series of steps.

In order to design the adsorption process, it is necessary to determine the optimal process parameters by examining the behavior of the injected gas during adsorption and simulating the same. As the adsorption equilibrium relationship formula, the loading ratio correlation (LRC) may be used, and as the rate relationship formula, the linear driving force (i) may be used.

The method of separating olefins and paraffins having the same number of carbon atoms from each other according to one embodiment of the present invention is characterized by using the adsorbent for equilibrium adsorption and rate adsorption of $C_{2-4}$ hydrocarbons. Additionally, the method for separating hydrocarbons having a different number of carbon atoms according to one embodiment of the present invention is characterized by using the adsorbent for equilibrium adsorption and rate adsorption of $C_{2-4}$ hydrocarbons.

At this time, in order to increase the adsorption amount of the gas adsorbed to the adsorbent, the mixed gas may be cooled or compressed before adsorption. In order to desorb the gas adsorbed to the adsorbent, the pressure may be lowered, the adsorbent may be heated, or a desorbent may be used.

Meanwhile, the present invention provides a method for separating olefins and paraffins having the same number of carbon atoms, including:
contacting a mixture of olefins and paraffins having the same number of carbon atoms in $C_{2-4}$ hydrocarbons with the organic-inorganic hybrid nanoporous material of the present invention.

Further, the present invention provides a method for separating hydrocarbons having a different number of carbon atoms, including:
contacting a mixture containing $C_{1-4}$ hydrocarbons having a different number of carbon atoms with the organic-inorganic hybrid nanoporous material of the present invention.

Furthermore, the present invention provides a method for separating olefin and paraffin gases from a mixed hydrocarbon gas, including:
contacting a mixed $C_{1-4}$ hydrocarbon gas with the organic-inorganic hybrid nanoporous material of the present invention.

In each of the separation methods, the adsorption-desorption temperature may be from −30° C. to 150° C., and the adsorption-desorption pressure may be from 0.1 bar to 35 bar, but these are not limited thereto.

For example, as shown in FIGS. 5 to 13, with respect to the olefins and paraffins having the same number of carbon atoms, the organic-inorganic hybrid nanoporous material of the present invention has a high adsorption capacity and/or adsorption rate selectively for olefins, although these can vary with temperature, pressure, and/or time under the same conditions during adsorption. This indicates that the organic-inorganic hybrid nanoporous material of the present invention can be used as an adsorbent to separate olefins from a mixture of olefins and paraffins having the same number of carbon atoms. In addition, it also indicates that the separation efficiency can be maximized by searching for conditions under which the differences in the adsorption capacity and/or adsorption rate are maximized by controlling the temperature, pressure, and/or time.

Further, in the series of $C_{2-4}$ hydrocarbon olefin and paraffin compounds, which have a different number of carbon atoms, the organic-inorganic hybrid nanoporous material of the present invention has different adsorption rates depending on the number of carbon atoms. Furthermore, there are the differences in adsorption rate in the order of ethylene >propylene >ethane >>propane for each of olefins and paraffins having a different number of carbon atoms, such as ethane, ethylene, propane, and propylene. Specifically, the organic-inorganic hybrid nanoporous material of the present invention exhibits a higher adsorption rate for olefins such as propylene and ethylene than for paraffins such as propane or ethane. This indicates that, by way of the organic-inorganic hybrid nanoporous material of the present invention, not only can the olefin series or paraffin series having a different number of carbon atoms be separated, but also, olefins and paraffins may be separated from a mixture in which they are mixed. Specifically, by using the adsorbent including the organic-inorganic hybrid nanoporous material of the present invention, at least one selected from the group consisting of ethylene, propylene, and butylene may be separated from a mixed hydrocarbon gas containing two or more olefins and paraffins selected from the group consisting of methane, ethane, ethylene, propane, propylene, butane, and butylene.

Moreover, the present invention provides a method for preparing $C_{2-4}$ olefins, including:
a first step of adsorbing olefins in $C_{2-4}$ hydrocarbons to an adsorbent including the organic-inorganic hybrid nanoporous material of the present invention; and
a second step of purging the adsorbent to which $C_{2-4}$ olefins are adsorbed with an inert gas.

As described above, the organic-inorganic hybrid nanoporous material of the present invention has a high adsorption capacity and/or adsorption rate selectively for $C_{2-4}$ olefins, and based on this, $C_{2-4}$ olefins may be separated from $C_{2-4}$ paraffins.

That is, when the mixture of $C_{2-4}$ hydrocarbons is brought into contact with the adsorbent including the organic-inorganic hybrid nanoporous material of the present invention in the first step, the $C_{2-4}$ olefins are selectively adsorbed in higher amounts according to the selectivity and remain in the adsorbent for a longer period of time, whereas $C_{2-4}$ paraffins are only partially adsorbed and pass through the adsorbent without further adsorption. Thus, the $C_{2-4}$ olefins may be prepared by desorbing and recovering the $C_{2-4}$ olefins from the adsorbent to which the $C_{2-4}$ olefins are adsorbed. At this time, the desorption of the $C_{2-4}$ olefins from the adsorbent may be achieved by applying a weak vacuum or purging with a non-condensable inert gas. Although the organic-inorganic hybrid nanoporous material of the present invention exhibits relatively high adsorption performance for $C_{2-4}$ olefins compared to $C_{2-4}$ paraffins, the adsorption energy for olefins is low, and thus, the $C_{2-4}$ olefins may be desorbed by applying a weak vacuum or purging with a non-condensable inert gas.

At this time, the inert gas in the second step may be applied at atmospheric pressure or higher, but is not limited thereto.

For example, the inert gas used in the second step may be nitrogen, helium, argon, or a mixed gas thereof, but is not limited thereto.

The inert gas refers to a "non-reactive gas", which does not react with $C_{2-4}$ olefins to be desorbed and recovered due to its very low reactivity, and may include any gas that has a role in desorbing and releasing the $C_{2-4}$ olefins bound to the adsorbent with a low adsorption energy by applying a gas flow, without limitation. Accordingly, the gas provided from the second stage may be in the form of a mixture including both the hydrocarbons which have escaped from the adsorbent, such as olefins, and the inert gas.

Therefore, in order to obtain high-purity olefins, a step of removing the inert gas from the mixture of the hydrocarbons which have escaped from the adsorbent and the inert gas, and separating and recovering the target hydrocarbons, i.e., olefins, may be further performed after the second step. For example, the step of separating and recovering olefins may be carried out by a pressure swing adsorption-desorption method, a pressure-vacuum swing adsorption-desorption method, a temperature swing adsorption-desorption method, a separation membrane separation method, a compressed gas-liquid separation method, a distillation method, or a combination thereof, but is not limited thereto. For example, since the inert gas has a higher condensing pressure than the $C_{2-4}$ olefins to be recovered, the olefins may be easily separated by compressing the mixed gas via a separation method and subjecting only the liquefied olefins to gas-liquid separation, or by applying a simple distillation method after gas-liquid separation, based on the fact that the $C_{2-4}$ olefins to be recovered are not liquefied by compression under the conditions of liquefaction. Further, since the molecular size of the inert gas is smaller than the molecular size of the $C_{2-4}$ olefins, high-purity $C_{2-4}$ olefins may be obtained by simple separation using a separation membrane according to the differences in the molecular size. Furthermore, the inert gas generally has an adsorptive strength lower than that of the $C_{2-4}$ olefins in the porous adsorbent, and thus, high-purity $C_{2-4}$ olefins may be obtained by easily separating the olefins through an additional adsorption separation process.

MODE FOR CARRYING OUT THE INVENTION

Hereinafter, the present invention will be described in more detail by way of Examples. However, these Examples are for illustrative purposes only, and the scope of the invention is not intended to be limited by these Examples.

Preparation Example 1: Preparation of MOF-Anhydride Adsorbent in the Presence of Ammonia as Nitrogen-Based Basic Additive The preparation of the adsorbent was initiated from the synthesis of a MOF base material. First, aluminum sulfate salt $Al_2(SO_4)3.18H_2O$ (1.02 g, 1.5 mmol) as an aluminum precursor and 1,2,4-benzenetricarboxylic acid (or trimellitic acid; TMA; 0.634 g, 3 mmol) were added to a 100 mL Teflon container, about 32 mL of distilled water was added thereto, and the mixture was stirred for 10 minutes. As a nitrogen-containing basic compound, ammonia water (29% aqueous solution, 0.176 g, 3.0 mmol) or dimethylformamide (DMF, 0.220 g to 0.309 g, 3.0 mmol to 4.2 mmol) was added to the solution, and the mixture was further stirred at room temperature for 30 minutes. Then, the Teflon container was placed in a stainless steel pressure reactor and tightly sealed to prevent the pressure from leaking. The temperature of a drying oven allowing for stirring was adjusted to 130° C., and the pressure reactor containing the solution was placed in the oven and allowed to react for 12 to 15 hours. The reaction temperature may be increased to 180° C. in order to control the yield and purity of the materials. After completion of the reaction, the reactor was cooled at room temperature, the solid products produced in the reactor and the remaining unreacted aluminum salt, sulfate anions, and TMA ligand were dispersed in distilled water and ethanol for separation, and the solid products were filtered through a vacuum filter and washed. The thus-obtained solid products were placed in a drying oven at 100° C. and dried for 6 hours to obtain a hybrid nanoporous material, and this product was named "Al-TMA(NP)" for convenience.

The Al-TMA(NP) obtained by the synthesis method above was heat-treated at a temperature of 400° C. under a vacuum of $10^{-4}$ Torr or less or a flow of an inert gas such as nitrogen, argon, or helium and allowed to stand in the air for more than 1 day to prepare a material, which was named "hydrated MOF-Anhydride", and this product was dried to prepare "dried MOF-Anhydride".

In order to obtain a specific surface area of Al-TMA(NP) and MOF-Anhydride, a physical adsorption isotherm of carbon dioxide was measured at dry ice temperature (−78° C.). The Al-TMA(NP) and MOF-Anhydride were each pretreated at a temperature of 200° C. under a vacuum of $10^{-4}$ Torr or less for 6 hours, and the physical adsorption isotherm of carbon dioxide was measured at −78° C. The adsorption of carbon dioxide did not occur in the Al-TMA(NP) because it had a small pore size, whereas the MOF-Anhydride showed an adsorption amount of 244 mL/g at $p/p_0$=0.9. The specific surface area calculated from the physical adsorption isotherm of carbon dioxide was 1080 m$^2$/g, and the pore volume was 0.46 cc/g.

X-ray diffraction analysis, thermogravimetric analysis, and infrared spectroscopy analysis were performed to confirm the structure and physiochemical properties of Al-TMA (NP) and MOF-Anhydride. First, the Al-TMA(NP) and MOF-Anhydride samples were added and the in situ X-ray diffraction patterns were obtained at an X-ray wavelength λ=0.7000 Å using an X-ray beam line manufactured by Pohang Accelerator Laboratory (PAL). The results are shown in FIG. 1. From these results, the composition and structure of the materials were analyzed. It was confirmed that the basic chemical composition of the hydrated Al-TMP (NP) corresponds to $\{Al(\mu_2\text{-}OH)[(CO_2)_2C_6H_3(COOH)]\}\cdot xH_2O$ (wherein x is an integer from 1 to 10), and that free COOH groups not bound to the aluminum ion were present at a ratio of 1 mole per 1 mole of aluminum in the skeleton. Further, it was confirmed from the analysis that the structure of hydrated Al-TMA(NP) was similar to the structure of Al-MIL-53, a solid having a small pore size reported in Loiseau et al., and that the unit lattice size was slightly larger and had the same space group Cc (Chem. Eur. J., 10: 1373 (2004)). Meanwhile, when analyzing the structure and chemical composition of the dried MOF-Anhydride, the most remarkable feature is that it contains an intramolecular anhydride functional group formed by condensation of two adjacent carboxylic acid groups on the aromatic compound of the skeleton. The chemical formula of the skeleton structure may be set as a nanoporous material containing the composition of $\{[C_6H_3(CO_2)C_2O_3]_a M_4(O)_b(OH)_c\}$ (wherein a, b, and c are each independently a rational number from 1 to 4).

The MOF-Anhydride includes an independent acid anhydride formed by intramolecular condensation of each benzene ring constituting the nanoporous skeleton. Despite the differences in the functional groups, it was confirmed that the space group of the skeleton structure in the MOF-Anhydride existed as Cc, identically with Al-TMP(NP). Further, it was confirmed that the size of the unit lattice of the hydrated MOF-Anhydride was similar to that of hydrated Al-TMA(NP), but in the dried MOF-Anhydride, considering that the size of the unit lattice was increased by more than 30%, it had skeleton flexibility.

In order to track the weight change of MOF-Anhydride and Al-TMP(NP) synthesized in the Preparation Example in accordance with temperature, the thermogravimetric analysis curves of the samples saturated with moisture at a relative humidity of 75% were obtained using a thermogravimetric analyzer (Infinity Pro, SINCO). The results are shown in FIG. 2. In the thermogravimetric curves of the hydrated MOF-Anhydride and Al-TMA(NP), the temperature was increased at a rate of 5° C./min using air as a transfer gas and the weight loss caused was measured. The structure and unit lattice size of the hydrated MOF-Anhydride and the hydrated Al-TMA(NP) were similar, but there were significant differences in the amount of moisture desorption and desorption temperature measured by thermogravimetric analysis. It was confirmed that not only were the amount of moisture desorption and thermal stability of the hydrated MOF-Anhydride higher than those of the hydrated Al-TMA (NP), but also, most of the moisture was desorbed at a relatively low temperature of 100° C. or less.

In order to identify the acid anhydride functional groups formed on the skeleton of the MOF-Anhydride synthesized according to the Preparation Example, the in situ infrared spectroscopy spectra were measured in a vacuum state, and the results are shown in FIG. 3. A self-supported IR thin film was prepared by compressing about 8 mg of powder into a size of 12 mm in diameter with a pressurization press using the hydrated MOF-Anhydride powder itself, without mixing with KBr used in the preparation of a specimen for conventional infrared analysis, and the thin film was mounted on an in situ infrared cell and treated at 200° C. for 1 hour or more under a vacuum of $1\times10^{-4}$ Torr to obtain infrared spectroscopy spectra. At this time, C=O stretching vibration peaks for the acid anhydride functional groups formed in the benzene ring were observed in the range of 1750 cm$^{-1}$ to 1950 cm$^{-1}$, and OH stretching vibration peaks of the OH functional groups present in the skeleton were observed in the range of 3500 cm$^{-1}$ to 3800 cm$^{-1}$.

Example 1: Single-Component $C_3$ Hydrocarbon Adsorption Characteristics of MOF-Anhydride Adsorbent An IGA (Intelligent Gravimetric Analyzer, Hiden Analytical Ltd.) adsorption apparatus was used to obtain adsorption-desorption isotherms of the single-component hydrocarbons in the MOF-Anhydride, which was dried after being synthesized according to the Preparation Example. Approximately 25 mg of MOF-Anhydride was placed on a mass scale equipped in the IGA adsorption apparatus and subjected to pretreatment by degassing at a temperature range of 100° C. to 450° C. under a vacuum of $10^{-4}$ Torr or less for 6 hours, depending on the type of hydrocarbons to be analyzed, and the adsorption pressure was varied from 0 atm to 10 atm, depending on the type of hydrocarbons, at an adsorption temperature ranging from 0° C. to 100° C. to obtain the single-component adsorption-desorption isotherms of propane, propylene, ethane, ethylene, n-butane, and iso-butene hydrocarbon molecules.

The adsorption-desorption isotherm curves for propane and propylene in the dried MOF-Anhydride measured at 50° C. are shown in FIG. 4. The adsorbent samples were vacuum-treated at 200° C. for 6 hours before measurement of the adsorption-desorption isotherms. As shown in FIG. 4, it was confirmed that the adsorption amount of propylene was always higher than that of propane from 0.2 atm to 5 atm. At 5 atm, as the adsorption amount of propylene was 4.44 mmol/g and the adsorption amount of propane was 3.64 mmol/g, the adsorption amount of propylene was higher by 0.80 mmol/g. The desorption isotherms of propylene and propane after adsorption were the same as those of the adsorption isotherms without hysteresis. From these results, it was confirmed that the adsorbed molecules were adsorbed by a weak interaction and thus were relatively easily desorbed.

Another feature observed together with the high adsorption amount and equilibrium adsorption selectivity for propylene relative to propane in the adsorption of $C_3$ hydrocarbons in the MOF-Anhydride was that the adsorbent exhibited a high working adsorption capacity for propylene. The working adsorption capacity is defined as the difference between the adsorption amount of a gas at the adsorption pressure and the adsorption amount of the same gas at the desorption pressure at the same adsorption temperature during gas separation by the pressure swing adsorption method. The working adsorption capacity measures the yield of purified gas per unit weight or unit volume, and can thus be an important criterion for determining adsorbent performance together with the absorption selectivity of the gas.

The working adsorption capacity of propylene in the MOF-Anhydride adsorbent was measured when the adsorption pressure of propylene at 50° C. was set to 5 atm and the desorption pressure was set to 1 atm or 0.5 atm. In the pressure swing adsorption process for gas separation, the pressure reduction of about 0.3 atm to 0.5 atm can be driven by a simple vacuum pump, an aspirator, or a gas ejector, which does not require much energy, and thus this can be regarded as an effective olefin/paraffin adsorption separation condition. Accordingly, the desorption pressure was set to 0.5 atm. The working adsorption capacity obtained was 1.40 mmol/g or more at 5 atm (adsorption)-0.5 atm (desorption), and 1.02 mmol/g at 5 atm (adsorption)-1 atm (desorption). These values are at least 5 times higher than the adsorption capacity of the conventional commercial adsorbent zeolite 13X and are analyzed to be much higher than those of MOF adsorbents applied to olefin separation.

In addition to $C_3$ hydrocarbons, adsorption-desorption isotherm curves for ethane and ethylene in the MOF-Anhydride were measured at 30° C. The adsorbent samples were pretreated at 100° C. for 6 hours before the measurement of the adsorption-desorption isotherms. As a result, the adsorption amount of ethylene from 0.2 atm to 10 atm was always higher than that of ethane, and at 30° C. and 10 atm, the adsorption amount of ethylene was 4.70 mmol/g and the adsorption amount of ethane was 4.07 mmol/g. In the case of ethylene, the desorption isotherm after adsorption was found to be the same as the adsorption isotherm without hysteresis. Thus, it can be confirmed that the adsorbed molecules were mostly present in a physically adsorbed form and could be easily desorbed.

The adsorption-desorption isotherm curves for n-butane, 1-butene, and iso-butene in the MOF-Anhydride were measured at 70° C. The adsorbent samples were pretreated at 300° C. for 6 hours before the measurement of the adsorption-desorption isotherms. As a result, the adsorption amounts of $C_4$ hydrocarbons from 0.2 atm to 2.5 atm were obtained in the order of iso-butene>1-butene>n-butane.

Example 2: Analysis of Hydrocarbon Adsorption Rate of MOF-Anhydride Adsorbent

In the measurement of the absorption-desorption isotherm curves of single-component hydrocarbons in the MOF-Anhydride according to Example 1, the adsorption amount was obtained after the adsorption reached the equilibrium state for each adsorption pressure during the data collection. From this process, it was confirmed that the time required to reach the equilibrium state in the adsorption of propylene was significantly different from that in the adsorption of propane. In order to further confirm the differences in the adsorption rate between propylene and propane under the same pressure, the differences in the diffusion rate between propylene and propane according to the adsorption temperature during adsorption were measured at 1 atm using an IGA (Intelligent Gravimetric Analyzer, Hiden Analytical Ltd.). After pretreating the adsorbent under the same conditions as in Example 1, the pressures of propylene and propane were adjusted to 1 atm, and the rate at which the adsorption amount increased according to time as propylene and propane diffused into the adsorbent pores was expressed as a diffusional time constant, and the unit was expressed as the reciprocal of time ($s^{-1}$).

FIG. 5 shows the comparative adsorption rate curve for propylene and propane in the MOF-Anhydride, which occurred at 50° C. and 1 atm for 600 seconds (10 minutes). As shown in FIG. 5, propylene was adsorbed almost linearly at a high rate from the initiation of adsorption until 60 seconds, and thereafter, the adsorption proceeded slowly until 300 seconds and reached near-equilibrium, and an adsorption amount of 3.19 mmol/g was obtained. In contrast, the adsorption of propane proceeded much more slowly than the adsorption of propylene, and the adsorption amount slowly increased without an inflection point from the beginning of adsorption until 600 seconds, and the adsorption amount of propane was only 0.88 mmol/g at 600 seconds. This indicates that the MOF-Anhydride adsorbent exhibited a much faster adsorption rate for propylene than for propane under given conditions. The diffusional time constants were calculated so as to compare the diffusion rates of propylene and propane in the MOF-Anhydride adsorbent based on the results obtained from the initial 150 seconds or less in the curve of FIG. 5. The diffusional time constant of propylene was $5.20 \times 10^{-4}$ $s^{-1}$, and the diffusional time constant of propane was $3.50 \times 10^{-6}$ $s^{-1}$. The adsorption rate separation selectivity of propylene/propane calculated from these results was about 150, which was very high.

Comparative Example 1: Adsorption Characteristics of Zeolite 13X Adsorbent

In order to compare the characteristics of the MOF-Anhydride adsorbent of the present invention with a conventional adsorbent, the adsorption characteristics of zeolite 13X, a commercial adsorbent, were measured.

The adsorption-desorption isotherms of propylene and propane in the zeolite 13X powder purchased from Sigma-Aldrich were measured. FIG. 6 shows the adsorption-desorption isotherms of propylene and propane in zeolite 13X measured at 50° C. under a pressure range of 0 atm to 5 atm. The adsorption amounts of propylene and propane at 5 atm were very high, with values of 3.3 mmol/g and 3.1 mmol/g, respectively. The working adsorption capacity was 0.15 mmol/g at 5 atm (adsorption)-1 atm (desorption), and the working adsorption capacity was 0.25 mmol/g at 5 atm (adsorption)-0.5 atm (desorption). These values were significantly lower than the working adsorption capacity of MOF-Anhydride, and there was a problem in constructing an effective adsorption separation technology because a desorption condition of high vacuum must be applied, or propylene and the desorbent must be separated by distillation after the adsorbed propylene was desorbed using a desorbent such as a $C_4$ hydrocarbon.

Further, in terms of the adsorption rate, there was almost no difference in the diffusion rate between propylene and propane adsorbed in zeolite 13X, and the equilibrium was reached in a short period of time; thus, it was confirmed that the zeolite 13X adsorbent was not suitable for the adsorption separation by rate difference, and was also not suitable for the rate separation due to a very slow desorption rate.

Comparative Example 2: Adsorption Characteristics of Hybrid Nanoporous Material ZIF-8 Adsorbent The $C_3$ hydrocarbon adsorption characteristics of a hybrid nanoporous material named ZIF-8, which, as a rate-selective adsorbent among the hybrid nanoporous materials, is known to have a high adsorption rate for propylene relative to propane, were measured and compared with those of the MOF-Anhydride adsorbent.

The ZIF-8 used to compare the adsorption characteristics was synthesized with reference to the method described in J. Am. Chem. Soc., 131: 10368-10369 (2009).

0.304 g of $Zn(NO_3)_2 \cdot 6H_2O$ was dissolved in 13.8 mL of methanol in a 50 mL beaker, and the mixture was stirred for 15 minutes. In another 50 mL beaker, 0.663 g of 2-methylimidazole was dissolved in 13.8 mL of methanol, and the mixture was stirred for 15 minutes. The two solutions were mixed slowly such that the final molar ratio of the reactants was Zn:2-methylimidazole:methanol=1:8:680. The reaction product was placed in a Teflon reaction vessel, stirred for 10 minutes, mounted in a microwave reactor, allowed to react at 150° C. for 1 hour, and then cooled to room temperature. The thus-obtained product was filtered using a centrifugal separator, and the thus-obtained crystals were washed with methanol to remove impurities and dried in an oven at 100° C. for 12 hours to obtain a final product.

X-ray diffraction pattern analysis, scanning electron microscopy analysis, and physical adsorption isotherm analysis of nitrogen at −196° C. were carried out to confirm characteristics such as the structure, particle size, and specific surface area of the synthesized organometallic skeleton compound (FIG. 7).

The adsorption isotherms of propylene and propane in the ZIF-8 adsorbent appeared to have the same form without significant difference. The adsorption amounts of propylene and propane at 5 atm were 3.60 mmol/g and 3.65 mmol/g, respectively. There was not much difference in the equilibrium adsorption amount between propylene and propane under the given measurement conditions, and thus, it can be seen that separation by equilibrium adsorption was difficult. In addition, the working adsorption capacity was as low as 0.50 mmol/g or less at 5 atm (adsorption)-1 atm (desorption) and at 5 atm (adsorption)-0.5 atm (desorption).

FIG. 7(c) shows a comparative curve of the adsorption rate between propylene and propane in ZIF-8, which occurred at 30° C. and 1 atm for 5 minutes. In FIG. 7(c), it can be seen that the adsorption rate of propane and the adsorption rate of propylene do not differ greatly, unlike those reported in the literature. The diffusional time constant of propylene according to crystal size was $6.44 \times 10^{-4}$ $s^{-1}$, and the diffusional time constant of propane was $7.00 \times 10^{-4}$ $s^{-1}$. The adsorption rate of propylene/propane calculated from the diffusional time constants showed little selectivity. According to the Jing Li group in the United States (J. Am. Chem. Soc., 131: 10368-10369 (2009)), the selectivity of ZIF-8 according to the diffusion rate coefficient of propylene relative to propane was as high as 125 at 30° C. The ZIF-8 adsorbent used herein was synthesized with a large particle size of 100 µm or more. In the Comparative Example, since a small particle size of 1 µm or less was used, the low adsorption rate selectivity was attributed to the small crystal size. As a result, the crystal size in ZIF-8 was considered as a factor that determined the selectivity of the adsorption rate.

Example 3: Adsorption Breakthrough Characteristics of Propylene and Propane in MOF-Anhydride Adsorbent An adsorption breakthrough apparatus equipped with a fixed bed adsorption column was prepared and used to separate propylene from a mixed gas of propylene/propane having a molar composition ratio of 40% to 60% by using the MOF-Anhydride synthesized according to Preparation Example 1. The flow rate of each gas was precisely controlled using MFC, and the pretreatment, reaction gas stabilization, and adsorption reaction were controlled using a 6-port valve to determine the flow direction. Silica having no reactivity was used in the upper part and lower part of the adsorbent layer to reduce the volume of the adsorbent layer. The reaction gas passing through the adsorbent was analyzed using a flame ionization detector (FID)-equipped gas chromatograph (GC) and a mass spectrometer. The separation of paraffins/olefins was analyzed using an alumina column of the GC.

The separation was carried out using a column-type reactor having a diameter of ¼ inch and a length of 30 cm prepared for the separation of propane/propylene. Adsorption conditions for separating propane/propylene were as follows: the adsorption was carried out at 30° C. to 70° C. under 1 atm to 5 atm, and 1.38 g of the MOF-Anhydride adsorbent molded into a sphere-like body having a size of 0.8 mm to 1.2 mm was used. The adsorbent was heated at 200° C. for 6 hours for pretreatment, cooled to the adsorption temperature, and purged with helium. Then, a mixed gas of propane/propylene (molar composition of 60 mol %:40 mol %) was injected into a breakthrough column equipped with an adsorbent at a flow rate of 80 mL/min to analyze the separation characteristics of propane and propylene.

Among the experimental results of the breakthrough separation of the mixed gas, repetitive adsorption breakthrough curves of propane and propylene were measured under conditions of 1 atm, 70° C., and a mixed gas flow rate of 50 cc/min. As a result, the breakthrough curve under the adsorption condition was detected at the outlet from about 40 seconds after the start of adsorption because the adsorption amount of propane was insignificant. In contrast, propylene was detected at the outlet from 170 seconds after adsorption, showing very high separation efficiency between these gases. In addition, the adsorbent after the adsorption breakthrough was easily recovered by the helium transfer gas, and breakthrough curves could be obtained with almost the same performance even in the breakthrough experiment in which the cycles were repeated 10 times.

Example 4: Hydrocarbon Adsorption Separation Characteristics of MOF-Anhydride Adsorbent In this embodiment, adsorption separation characteristics of hydrocarbons having a different number of carbon atoms in the MOF-Anhydride adsorbent were compared. When the adsorption rates of ethane/propane/n-butane were compared with the adsorption rates of ethylene/propylene/iso-butene at 70° C. and 1 atm, in the case of the MOF-Anhydride adsorbent, it was confirmed that the adsorption rate decreased as the number of carbon atoms in the hydrocarbon increased. The adsorption rates of paraffin hydrocarbons at the same adsorption temperature and pressure were in the order of ethane>propane>n-butane, and the adsorption rates of olefinic hydrocarbons were in the order of ethylene>propylene>iso-butylene, confirming that there were differences in the adsorption rate between olefins and paraffins. In addition, the adsorption rates of ethane, propane, ethylene, and propylene at the same adsorption temperature and pressure were compared, and as a result, the differences in the adsorption rate were observed in the order of ethylene>propylene>>ethane>propane. In particular, since the differences in the rate between propylene and ethane were considerably large, it was possible to obtain a method of separating the olefin gas and the paraffin gas from each other by utilizing these characteristics.

Example 5: Desorption and Recovery Characteristics of MOF-Anhydride Adsorbent Using Nitrogen In this Example, the effect of purging with inert nitrogen gas as a desorbing gas instead of using a vacuum was observed in the desorption step for separating propylene from a mixed gas of propane/propylene (60 mol %:40 mol %) using the MOF-Anhydride adsorbent synthesized according to Production Example 1 and recovering the adsorbent. Specifically, the experiment was conducted using the same adsorption breakthrough apparatus and conditions as in Example 3. The separation was carried out using a column-type reactor having a diameter of ¼ inch and a length of 30 cm prepared for the separation of propane/propylene. Adsorption conditions for separating propane/propylene were as follows: the adsorption was carried out at 70° C. under 5 atm, and 1.38 g of the MOF-Anhydride adsorbent molded into a sphere-like body having a size of 0.8 mm to 1.2 mm was used. The adsorbent was heated at 200° C. for 6 hours for pretreatment, cooled to 70° C., and purged with nitrogen. Then, the mixed gas of propane/propylene (60 mol %:40 mol %) was injected into a breakthrough column equipped with an adsorbent at a flow rate of 50 mL/min to analyze the separation characteristics of propane and propylene.

FIG. 8 shows the adsorption breakthrough curves measured under the condition of the rate-selective breakthrough separation of the mixed gas. From this, the adsorption amounts of propylene and propane in the adsorbent were calculated, and the adsorption amounts of 2.99 mmol/g and 0.45 mmol/g were obtained, respectively. After the adsorption breakthrough separation experiment, when nitrogen was supplied at a flow rate of 45 mL/min at 70° C. for 10 minutes, and the mixed gas of propane/propylene (60 mol %:40 mol %) was again subjected to a second adsorption breakthrough experiment at a flow rate of 50 mL/min at 70° C. and 5 atm, the adsorption amounts of 2.37 mmol/g and 0.37 mmol/g were obtained for propylene and propane, respectively, which were slightly lower than the adsorption amounts obtained in the first breakthrough experiment. In addition, when the desorption was repeated using nitrogen and then third and fourth breakthrough experiments were conducted, the results of the separation were similar to those of the second adsorption breakthrough curve. From these results, it was confirmed that separation could be effectively performed even when nitrogen gas was used. These results support that an inert desorption gas could be used instead of vacuum as means of desorbing the olefin adsorbent.

Preparation Example 2: Synthesis of Al-TMA(NP) Absorbent 3 mmol of an aluminum salt ($AlCl_3 \cdot 6H_2O$) and 3 mmol of 1,2,4-benzenetricarboxylic acid (or trimellitic acid, TMA) were added to a Teflon reactor, and distilled water was added thereto to adjust the concentration of the reaction solution such that the final molar ratio of the reactant solution was Al:TMA:$H_2O$=1:1:590. The solution was mixed at room temperature for 30 minutes using a magnetic stirrer, and the reactor containing the reactant solution was maintained at a temperature range of 170° C. to 200° C. for 12 hours to perform crystallization. The pH of the solution before the reaction was 1.10, and the pH of the solution after completion of the reaction was 0.85. After completion of the reaction, the reactor was cooled at room temperature, the solid product produced in the reactor was recovered, and in order to separate the remaining unreacted aluminum salt, chlorine anions, and 1,2,4-benzenetricarboxylic acid ligand from the solid product crystals, the solid product was filtered and washed through a filter using distilled water. Then, the product was further filtered and purified using distilled water and ethanol at a temperature range of 60° C. to 80° C., and crystals were recovered using a vacuum filter. The thus-recovered crystals were dried again at 100° C. to obtain an Al-TMA(NP) hybrid nanoporous material.

X-ray diffraction analysis, thermogravimetric analysis, and infrared spectroscopy analysis were performed to confirm the structure and physiochemical properties of Al-TMA (NP). First, X-ray diffraction patterns of hydrated Al-TMA (NP) samples were obtained using an X-ray diffractometer (Rigaku Diffractometer D/MAX IIIB, Ni-filtered Cu Kα radiation). In the X-ray diffraction patterns, two center peaks were obtained at 2θ=9.35° and 2θ=11.36°. It was confirmed that these X-ray diffraction patterns were similar to the X-ray diffraction pattern of Al-MIL-53-COOH material reported in Reimer et al. Cryst Eng Comm, 14: 4119 (2012). Further, it was analyzed that the Al-TMA(NP) had a different unit lattice size than the solid structure having narrow pores named Al-MIL-53(np) disclosed in Loiseau et al. Eur. J., 10: 1373 (2004), but had the same space group Cc.

In order to track the weight change of the Al-TMP(NP) absorbent obtained in the Preparation Example according to temperature, the thermogravimetric analysis curves of the samples saturated with moisture at a relative humidity of 75% were obtained using a thermogravimetric analyzer (Infinity Pro, SINCO). In the thermogravimetric curves of the hydrated Al-TMA(NP), the temperature was increased at a rate of 5° C./min using air as a transfer gas and the weight loss caused was measured. As a result, there was a primary weight loss of about 6.3 wt % in the temperature range of 230° C. to 250° C., followed by a secondary weight loss of about 8.0 wt % at a temperature up to 450° C. Finally, at a temperature of 450° C. or higher, the structure collapsed and a weight loss of about 67.0 wt % was observed as $Al_2O_3$ was formed. It is believed that the primary weight loss was due to the desorption of water molecules in the pores of the Al-TMA(NP) material, and that the secondary weight loss was due to the decomposition of the free COOH groups bound to the organic ligand of the skeleton or by dehydration condensation occurring at two adjacent COOH groups, leading to the formation of a new chemical composition structure represented by Chemical Formula 2. Hereinafter, for convenience, the material represented by Chemical Formula 2 is shown as Al-TMA(NP)-HT.

In order to measure the specific surface area of the Al-TMA(NP)-HT material obtained through the heat treatment above, instead of the BET surface area calculation by a general physical adsorption isotherm measurement of nitrogen at −196° C., the physical adsorption isotherm of carbon dioxide at a dry ice temperature (−78° C.) was measured and calculated. This was because the structure of the Al-TMA(NP)-HT material contracted and became rigid at the low temperature of −196° C., and the nitrogen molecules were not sufficiently adsorbed, such that an accurate physical adsorption amount and specific surface area could not be measured. Thus, the surface area was calculated from the physical adsorption isotherm of carbon dioxide at a higher temperature. The Al-TMA(NP)-HT material was further heat-treated at 200° C. for 6 hours under a vacuum of $10^{-4}$ Torr or less, and subsequently, the physical adsorption isotherm of carbon dioxide was obtained. The specific surface area calculated therefrom was 1180 $m^2/g$, and the pore volume was 0.41 cc/g.

In addition, it was confirmed that the basic chemical composition of the Al-TMA(NP) material obtained by elemental analysis using ICP-MS (Inductively Coupled Plasma-Mass Spectrometry) and EDS (Energy Dispersive Spectrometer), structural analysis by X-ray diffraction pattern, thermogravimetric analysis, infrared spectroscopy analysis, and the like corresponded to $\{Al(\mu_2\text{-}OH)[(CO_2)_2C_6H_3(COOH)]\}\cdot mH_2O$ (m=0 to 10), and that the free COOH groups that did not bind to the aluminum ion of the skeleton were present in a ratio of 1 mole per 1 mole of aluminum. It was also confirmed that when the Al-TMA(NP) material was treated at a temperature of 100° C. or more and 450° C. or less, it had a chemical composition of $\{Al_4(\mu_2\text{-}OH)_4[(CO_2)_2C_6H_3(COOH)]_4\}_x\cdot\{Al_4(\mu_2\text{-}OH)_4[C_6H_4(CO_2)_2]_4\}_y\cdot\{Al_4(\mu_2\text{-}O)_d(\mu_2\text{-}OH)_e[(CO_2)C_6H_3(CO_2)O]_4\}$ (wherein x+y+z=1; x>0; y≥0; z≥0 (with the proviso that y=z=0 is excluded); 0≤d≤4; 0≤e≤4; and d, e, x, y, and z are rational numbers) through drying, dehydration condensation, decarboxylation, and the like.

Example 6: Single-Component Hydrocarbon Adsorption Characteristics of Al-TMA(NP)-HT Adsorbent The adsorption-desorption isotherms of the hydrocarbon compounds were obtained in the same manner as in Example 1 except that the Al-TMA(NP)-HT material synthesized in Preparation Example 2 was used.

For example, the adsorption-desorption isotherm curves for propane and propylene in the Al-TMA(NP)-HT were measured at 70° C. As the adsorbent samples, the Al-TMA(NP)-HT samples were pretreated at 200° C. for 6 hours before the measurement of the adsorption-desorption isotherms. As a result, it was confirmed that the adsorption amount of propylene was always higher than that of propane from 0.2 atm to 5 atm. At 5 atm, as the adsorption amount of propylene was 4.43 mmol/g and the adsorption amount of propane was 3.66 mmol/g, the obtained adsorption amount of propylene was higher by 0.77 mmol/g. The desorption isotherms of propylene and propane after adsorption were the same as those of the adsorption isotherms without hysteresis, confirming that most of the adsorbed molecules were present in a physically adsorbed form and thus could be relatively easily desorbed. Further, the same experiment was carried out by varying the temperature and/or type of hydrocarbons. Although there was a slight difference, similar adsorption patterns were observed even when the temperature was changed, and when the number of carbon atoms was changed from ethylene and ethane to butylene and butane, similar patterns were exhibited.

Meanwhile, from the adsorption-desorption isotherms of $C_3$ hydrocarbons according to the adsorption temperature, it was observed that the adsorption amount of propylene was 4.91 mmol/g and the adsorption amount of propane was 4.21 mmol/g at 30° C. and 5 atm, the adsorption amount of propylene was 4.73 mmol/g and the adsorption amount of propane was 3.99 mmol/g at 50° C. and 5 atm, and the adsorption amount of propylene was 4.11 mmol/g and the adsorption amount of propane was 3.45 mmol/g at 90° C. and 5 atm.

Table 1 shows the working adsorption capacity of propylene in the Al-TMA(NP)-HT adsorbent when the adsorption pressure of propylene was set to 5 atm and the desorption pressure was set to 1 atm or 0.5 atm. In the pressure swing adsorption process for gas separation, the pressure reduction of about 0.3 atm to 0.5 atm can be driven using a simple vacuum pump, an aspirator, or a gas ejector, which does not require much energy, and thus can be regarded as an effective olefin/paraffin adsorption separation condition. Accordingly, the desorption pressure was set at 0.5 atm. As shown in Table 1, the working adsorption capacity increased from 0.79 mmol/g to 1.25 mmol/g as the adsorption temperature increased from 30° C. to 90° C. at 5 atm (adsorption)-1 atm (desorption), and increased from 1.12 mmol/g to 1.71 mmol/g at 5 atm (adsorption)-0.5 atm (desorption). The working adsorption capacity of 1 mmol/g or more at 5 atm (adsorption)-1 atm (desorption) was at least 5 times higher than the adsorption capacity of the conventional commercial adsorbent zeolite 13X and is analyzed to be much higher than those of MOF adsorbents applied to olefin separation.

TABLE 1

| Adsorption temperature (° C.) | Working adsorption capacity (mmol/g) At 5 atm (adsorption) - 1 atm (desorption) | Working adsorption capacity (mmol/g) At 5 atm (adsorption) - 0.5 atm (desorption) |
|---|---|---|
| 30 | 0.79 | 1.12 |
| 50 | 0.99 | 1.37 |
| 70 | 1.10 | 1.52 |
| 90 | 1.25 | 1.71 |

Example 7: Analysis of Hydrocarbon Adsorption Rate of Al-TMA(NP) Adsorbent

The adsorption rates of the hydrocarbon compounds were analyzed in the same manner as in Example 2, except that the Al-TMA(NP)-HT material synthesized in Preparation Example 2 was used.

For example, the adsorption rates of propylene and propane in the Al-TMA(NP)-HT, which occurred at 70° C. and 1 atm for 600 seconds (10 minutes), were compared. As a result, in the comparative curve showing the adsorption rates of propylene and propane, propylene was adsorbed almost linearly at a high rate from the initiation of adsorption until 150 seconds, and thereafter, the adsorption proceeded slowly until 600 seconds and reached near-equilibrium at 600 seconds, and an adsorption amount of 2.65 mmol/g was obtained. In contrast, the adsorption of propane proceeded much more slowly than the adsorption of propylene, and the adsorption amount slowly increased without an inflection point from the beginning of adsorption until 600 seconds, and the adsorption amount of propane was 0.95 mmol/g at 600 seconds. These results indicate that the Al-TMA(NP)-HT adsorbent exhibited a much faster adsorption rate of propylene compared to that of propane under given conditions. When the diffusional time constants of the gases to be adsorbed were calculated, the diffusional time constant of propylene was $5.30 \times 10^{-4}$ s$^{-1}$, and the diffusional time constant of propane was $5.30 \times 10^{-6}$ s$^{-1}$. The adsorption rate separation selectivity of propylene/propane calculated from these results was about 100, which was very high. Further, it was observed that the adsorption rate separation selectivity of propylene/propane at 30° C. was 140, and the adsorption rate separation selectivity of propylene/propane at 50° C. was 200.

In order to compare the adsorption rates of $C_2$ and $C_4$ hydrocarbons with respect to the Al-TMA(NP)-HT adsorbent, the differences in the diffusion rate between ethylene and ethane and n-butane, 1-butene, and iso-butene were each measured during adsorption at 30° C. and 70° C. and 1 atm. As a result, the adsorption rate of ethylene in the Al-TMA(NP)-HT adsorbent was about 35 times higher than that of ethane, and the adsorption rates of 1-butene and iso-butene were about 5 to 12 times higher than that of n-butane.

Example 8: Adsorption Breakthrough Characteristics of Propylene and Propane in Al-TMA(NP)-HT Adsorbent The adsorption breakthrough characteristics of propylene and propane were analyzed in a similar manner as in Example 3 above, except that a fixed bed adsorption column equipped with the Al-TMA(NP)-HT adsorbent synthesized in Production Example 2 was used and that a propylene: propane=1:1 mixed gas was used.

The results of the breakthrough experiment of the mixed gas showed that propane was detected at the outlet at the same time as the adsorption because the adsorption amount of propane was insignificant under the adsorption condition of 1 atm. In contrast, propylene was detected at the outlet from 15 seconds after adsorption, showing very high separation efficiency. In addition, when the pressure was 5 atm, propane was detected at the outlet from 17 seconds after adsorption, and propylene was detected at the outlet after 30 seconds. Although the separation efficiency at 5 atm was slightly lower compared to the pressure condition at 1 atm, it was confirmed that the adsorption breakthrough separation occurred even at 5 atm.

Example 9: Adsorption Separation Characteristics of Hydrocarbons in Al-TMA(NP)-HT Adsorbent The adsorption separation characteristics of other hydrocarbons were measured in a similar manner as in Example 4 using the Al-TMA(NP)-HT adsorbent synthesized in Preparation Example 2. For example, in the graph showing the adsorption rates of ethane/propane/n-butane and ethylene/propylene/iso-butene at 70° C. and 1 atm, the Al-TMA(NP)-HT adsorbent was pretreated at 200° C. for 6 hours before the measurement of the adsorption rate for each molecule. The adsorption rate of the Al-TMA(NP)-HT adsorbent decreased as the number of carbon atoms in the hydrocarbons increased. The adsorption rates of paraffin hydrocarbons at the same adsorption temperature and pressure were in the order of ethane>propane>n-butane, and the adsorption rates of olefin hydrocarbons were in the order of ethylene>propylene>iso-butylene, confirming that there were differences in the adsorption rate. In addition, the adsorption rates of ethane, propane, ethylene, and propylene at the same adsorption temperature and pressure were compared, and as a result, the differences in the adsorption rate were observed in the order of ethylene>propylene>ethane>propane. In particular, since the differences in the rate of propylene and ethane were considerably large, from these results it was found that the olefins and the paraffins could be separated.

The invention claimed is:

1. An organic-inorganic hybrid nanoporous material comprising:

a nanoporous skeleton structure having an aromatic portion, the nanoporous skeleton structure including coordinate bonds between organic ligands containing aromatic portions to central metal ions, at least some of the aromatic portions being bonded to intramolecular acid anhydride functional groups in which an independent COOH functional group, which is not coordinated to a metal ion, in a benzenetricarboxylic acid organic ligand coordinated to a trivalent central metal ion is present and which contains the composition of Chemical Formula 2, or a hydrate or solvate thereof:

$A_x B_y C_z$      [Chemical Formula 2]

$A=\{M_4(\mu_2\text{-}OH)_4[(CO_2)_2C_6H_3COOH]_4\}$
$B=\{M_4(\mu_2\text{-}OH)_4[C_6H_4(CO_2)_2]_4\}$
$C=\{M_4(\mu_2\text{-}O)_d(\mu_2\text{-}OH)_e[(CO_2)C_6H_3(CO)_2O]_4\}$ in Chemical Formula 2, M=a trivalent metal ion; x+y+z=1; x>0; y≥0; z≥0 (with the proviso that y=z=0 is excluded); 0≤d≤4; 0≤e≤4; and d, e, x, y, and z are rational numbers.

2. The organic-inorganic hybrid nanoporous material of claim 1,
wherein at least a portion of the skeleton structure is represented by Chemical Formula 1 below, or a hydrate or solvate thereof:

$\{[C_6H_3(CO_2)C_2O_3]_a M_4(O)_b(OH)_c\}$      [Chemical Formula 1]

in Chemical Formula 1, M is a trivalent metal ion, and a, b, and c are each independently a rational number from 0 to 4.

3. The organic-inorganic hybrid nanoporous material of claim 1, wherein the organic-inorganic hybrid nanoporous material represented by Chemical Formula 2 is prepared by synthesizing a hybrid nanoporous material using a trivalent metal ion salt and a 1,2,4-benzenetricarboxylic acid ligand as reaction raw materials and allowing for heat treatment at a temperature of 100° C. to 450° C.

4. An apparatus for adsorption separation of $C_{2-4}$ hydrocarbons, comprising the organic-inorganic hybrid nanoporous material of claim 1 as an adsorbent.

5. A method for separating olefins and paraffins having the same number of carbon atoms, comprising:
contacting a mixture of olefins and paraffins having the same number of carbon atom in $C_{2-4}$ hydrocarbons with the organic-inorganic hybrid nanoporous material of claim 1, wherein the adsorption-desorption temperature is from −30° C. to 150° C. and the adsorption-desorption pressure is from 0.1 bar to 35 bar.

6. The method for separating olefins and paraffins having the same number of carbon atoms of claim 5, wherein the organic-inorganic hybrid nanoporous material of claim 1 is the organic-inorganic hybrid nanoporous material of claim 2.

7. A method for separating hydrocarbons having a different number of carbon atoms, comprising:
contacting a mixture containing $C_{1-4}$ hydrocarbons having a different number of carbon atoms with the organic-inorganic hybrid nanoporous material of claim 1,
wherein the adsorption-desorption temperature is from −30° C. to 150° C. and the adsorption-desorption pressure is from 0.1 bar to 35 bar.

8. The method for separating hydrocarbons having a different number of carbon atoms of claim 7,
wherein the organic-inorganic hybrid nanoporous material of claim 1 is the organic-inorganic hybrid nanoporous material of claim 2.

9. A method for separating olefin and paraffin gases from a mixed hydrocarbon gas, comprising:
contacting a mixed $C_{1-4}$ hydrocarbon gas with the organic-inorganic hybrid nanoporous material of claim 1,
wherein the adsorption-desorption temperature is from −30° C. to 150° C. and the adsorption-desorption pressure is from 0.1 bar to 35 bar.

10. The method for separating olefin and paraffin gases from a mixed hydrocarbon gas of claim 9,
wherein the organic-inorganic hybrid nanoporous material of claim 1 is the organic-inorganic hybrid nanoporous material of claim 2.

11. A method for preparing $C_{2-4}$ olefins, comprising:
a first step of adsorbing olefins in $C_{2-4}$ hydrocarbons to an adsorbent including the organic-inorganic hybrid nanoporous material of claim 1; and
a second step of purging the adsorbent to which $C_{2-4}$ olefins are adsorbed with an inert gas.

12. The method for preparing $C_{2-4}$ olefins of claim 11, wherein the inert gas in the second step is nitrogen, helium, argon, or a mixed gas thereof.

13. The method for preparing $C_{2-4}$ olefins of claim 11, wherein the organic-inorganic hybrid nanoporous material of claim 1 is the organic-inorganic hybrid nanoporous material of claim 2.

14. A method for preparing the organic-inorganic hybrid nanoporous material of claim 1, comprising:
a first step of preparing a mixed solution of a trivalent metal ion-containing metal precursor, an organic ligand containing an aromatic compound substituted with two or more carboxylic acid functional groups, and a nitrogen-containing basic compound in a reaction vessel;
a second step of placing the reaction vessel in a pressure reactor and allowing to react at 100° C. to 200° C. for 10 to 20 hours; and
a third step of heat-treating the solid product obtained from the previous step at a temperature of 350° C. to 500° C.

15. An organic-inorganic hybrid porous material comprising:
a porous skeleton structure including a trivalent central metal ion and organic ligand coordination compound, the coordination compound including an aromatic portion, and an intramolecular acid anhydride functional group being bonded to the aromatic portion represented by the composition of Chemical Formula 2, or a hydrate or solvate thereof:

$$A_xB_yC_z \qquad \text{[Chemical Formula 2]}$$

A={$M_4(\mu_2\text{-OH})_4[(CO_2)_2C_6H_3COOH]_4$}; B={$M_4(\mu_2\text{-OH})_4[C_6H_4(CO_2)_2]_4$}; C={$M_4(\mu_2\text{-O})_d(\mu_2\text{-OH})_e[(CO_2)C_6H_3(CO)_2O]_4$}; M=a trivalent ion; x+y+z=1; x>0; y≥0; z≥0 (with the proviso that y=z=0 is excluded); 0≤d≤4; 0≤e≤4; and d, e, x, y, and z are rational numbers.

16. The organic-inorganic hybrid porous material of claim 15 wherein the trivalent central metal ion is an aluminum ion.

17. The organic-inorganic hybrid nanoporous material of claim 2 wherein the trivalent central metal ions are $Al^{3+}$.

* * * * *

UNITED STATES PATENT AND TRADEMARK OFFICE
CERTIFICATE OF CORRECTION

| | | |
|---|---|---|
| PATENT NO. | : 11,285,455 B2 | |
| APPLICATION NO. | : 16/342937 | |
| DATED | : March 29, 2022 | |
| INVENTOR(S) | : Ji Woong Yoon et al. | |

It is certified that error appears in the above-identified patent and that said Letters Patent is hereby corrected as shown below:

In the Claims

Column 28, Line 25, Claim 1:
After "organic ligands containing aromatic portions to"
Insert -- trivalent --.

Column 30, Line 29, Claim 15:
After "[Chemical Formula 2]"
Insert -- wherein --.

Signed and Sealed this
Second Day of August, 2022

Katherine Kelly Vidal
*Director of the United States Patent and Trademark Office*